US007063847B1

(12) United States Patent
Sanderson et al.

(10) Patent No.: US 7,063,847 B1
(45) **Date of Patent: *Jun. 20, 2006**

(54) COMPOSITIONS AND METHODS FOR ENHANCING IMMUNE RESPONSES MEDIATED BY ANTIGEN-PRESENTING CELLS

(75) Inventors: Sam D. Sanderson, Omaha, NE (US); Michael A. Hollingworth, Omaha, NE (US); Richard M. Tempero, Seattle, WA (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,922

(22) Filed: May 5, 2000

Related U.S. Application Data

(63) Continuation-in-part of application No. 09/051,685, filed as application No. PCT/US96/16825 on Oct. 18, 1996.

(60) Provisional application No. 60/005,727, filed on Oct. 20, 1995.

(51) Int. Cl.
*A61K 39/00* (2006.01)
*A61K 39/38* (2006.01)

(52) U.S. Cl. .............................. 424/184.1; 424/185.1; 424/192.1; 530/350; 530/388.2

(58) Field of Classification Search ............ 424/184.1, 424/185.1, 192.1; 530/350, 388.2
See application file for complete search history.

(56) References Cited

U.S. PATENT DOCUMENTS 5,262,303 A 11/1993 Sipe et al.
5,506,120 A * 4/1996 Yamamoto et al.
5,696,230 A 12/1997 Sanderson
5,827,666 A 10/1998 Finn et al.
5,955,073 A * 9/1999 Rybak et al.
5,976,546 A 11/1999 Laus et al.
5,989,552 A * 11/1999 McKenzie et al.
6,146,631 A * 11/2000 Better et al.
6,248,352 B1 * 6/2001 Romet-Lemonne et al.

FOREIGN PATENT DOCUMENTS

EP 0 145 174 6/1985
GB 2 117 514 A 10/1983
WO WO 92/05793 4/1992
WO WO 92/11031 7/1992
WO WO 93/10814 6/1993
WO WO 95/25957 9/1995
WO WO 96/22377 A1 7/1996

OTHER PUBLICATIONS

Buchner, R., et al., *Characterization of Site-Directed Neutralizing Antibodies Specific for a Peptide $_k$R(33) Derived from the Predicted Amino Terminal Region of the Human $_k$ Receptor*, The American Association of Immunologists, 1997, pp. 0022-1767.

Dempsey, P., et al., *C3d of Complement as a Molecular Adjuvant: Bridging Innate and Acquired Immunity*, Science, vol. 271, Jan. 1996, pp. 348-350.

Ember, J., et al., *Biologic Activity of Synthetic Analogues of C5a Anaphylatoxin*, The Journal of Immunology, vol. 148, No. 10, May 15, 1992, pp. 3165-3173.

Goodman, M., et al., *Potentiation of the Primary Humoral Immune Response in Vitro By C5a Anaphylatoxin*, The Journal of Immunology, vol. 129, No. 1, Jul. 1982, pp. 70-75.

Hobbs, M., et al., *Induction of Human B Cell Differentiation by Fc Region Activators*, Clinical Immunology and Immunopathology, vol. 50, 1989, pp. 251-263.

Morgan, E., *Regulaton of Human B Lymphocyte Activation by Opoid Peptide Hormones Inhibition of IgG Production by Opioid Receptor Class (μ-, κ-, δ-) Selective Agonists*, Journal of Neuroimmunology, vol. 65, 1 1996, p. 21-30.

Morgan, E., et al., *Characterization of Neutralizing Antibodies Specific for a Peptide, C5aR- (9-29) , Derived from the Predicted Amino-Terminal Sequence of the Human C5a Receptor*, The Journal of Immunology, vol. 151, No. 1, Jul. 1, 1993, pp. 377-388.

Rammensee, H-G., et al., *Peptides Naturally Presented by MHC Class I Molecules*, Annu. Rev. Immunol., vol. 11, 1993, pp. 213-244.

Sanderson, S., et al., *Decapeptide Agonists of Human C5a: The Relationship between Conformation and Spasmogenic and Platelet Aggregatory Activities*, Journal of Medicinal Chemistry, vol. 37, No. 19, 1994, pp. 3171-3180.

Tempero, R., et al., *Molecular Adjuvant Effects of a Conformationally Biased Agonist of Human C5a Anaphylatoxin*, The Journal of Immunology, 1997, pp. 1377-1382.

(Continued)

*Primary Examiner*—G. R. Ewoldt
(74) *Attorney, Agent, or Firm*—Dann Dorfman Herrell and Skillman; Kathleen D. Rigaut; Robert C. Netter, Jr.

(57) ABSTRACT

Molecular adjuvants are disclosed comprising an antigen presenting cell-targeting ligand linked to an immunogen, e.g. tumor associated antigens, bacterial or viral antigens. The ligand and the immunogen are linked via a cleavable linker such as a protease-sensitive oligopeptide, to facilitate processing of the adjuvant by the antigen presenting cell. Methods are disclosed for delivery of these molecular adjuvants to patients, resulting in the transduction of activating signals to the targeted antigen presenting cell, thereby enhancing the immune response to the co-delivered immunogen.

15 Claims, 5 Drawing Sheets

OTHER PUBLICATIONS

Barclay et al., "GM-CSFR, Granulocyte-Macrophage Colongy-Stimulating Factor Receptor." The Leucocyte Antigen Facts Book, 1997, Second Edition, Academic Press, London.
Guyre et al., "Monoclonal Antiboides that Bind to Distinct Epitopes on FcγRI are Able to Trigger Receptor Function." The Journal of Immunoogy, 1989, pp. 1650-1655, vol. 143, No. 5.
Kennedy et al., "Protein-Protein Coupling Reactions and the Applications of Protein Conjugates." Clinica Chimica Acta, 1976, pp. 1-31, vol. 70.
Baier, G. et al. "Immunogenic Targeting of Recombinant Peptide Vaccines to Human Antigen-Presenting Cells by Chimeric Anti-HLA-DR and Anti-Surface Immonoglobulin D Antibody Fab Fragments In Vitro"; Journal of Virology, 69(4): 2357-2365 (1995).
Ember, J.A. et al. "Biologic Activity of Synthetic Analogues of C5a Anaphylatoxin"; Journal of Immunology, 148; 3165-3173 (1992).
Sanderson, S.D. et al. "Decapeptide Agonists of Human C5a: The Relationship between Conformation and Spasmogenic and Platelet Aggregatory Activities"; J. Med. Chem., 37: 3171-3180 (1994).
Tempero, R.M. et al. "Molecular Adjuvant Effects of a Conformationally Biased Agonist of Human C5a Anaphylatoxin"; The Journal of Immunology, 158: 1377-1382 (1997).
Sanderson, S.D. et al. "Decapeptide Agonists of Human C5a: The Relationship between Conformation and Neutrophil Response"; J. Med. Chem., 38: 3669-3675 (1995).

* cited by examiner

```
                              SEQUENCE LISTING

<160> NUMBER OF SEQ ID NOS: 20

<210> SEQ ID NO 1
<211> LENGTH: 10
<212> TYPE: PRT
<213> ORGANISM: Artificial sequence
<220> FEATURE:
<223> OTHER INFORMATION: Ala is d-Ala
<220> FEATURE:
<221> NAME/KEY: VARIANT
<222> LOCATION: (9)..(9)
<223> OTHER INFORMATION: Ala is d-Ala
<220> FEATURE:
<221> NAME/KEY: MISC_FEATURE
<223> OTHER INFORMATION: Synthetic Sequence

<400> SEQUENCE: 1

Tyr Ser Phe Lys Pro Met Pro Leu Ala Arg
1               5                   10


<210> SEQ ID NO 2
<211> LENGTH: 19
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (18)..(18)
<223> OTHER INFORMATION: Ala is d-Ala

<400> SEQUENCE: 2

Tyr Lys Gln Gly Gly Phe Leu Gly Leu Tyr Ser Phe Lys Pro Met Pro
1               5                   10                  15

Leu Ala Arg


<210> SEQ ID NO 3
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 3

His Gly Thr Val Ile Glu Ser Leu Glu Ser Leu Asn Asn Tyr Phe Asn
1               5                   10                  15

Phe Phe Gly Ile Asp Val Glu Glu Lys Ser Leu Phe Leu Asp Ile Trp
            20                  25                  30

Arg Asn Trp Gln Lys Asp Gly
        35


<210> SEQ ID NO 4
<211> LENGTH: 39
```

<212> TYPE: PRT
<213> ORGANISM: Artificial sequence
<220> FEATURE:
<223> OTHER INFORMATION: Synthetic sequence

<400> SEQUENCE: 4

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu
        35
```

<210> SEQ ID NO 5
<211> LENGTH: 18
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (9)..(9)
<223> OTHER INFORMATION: Ala is d-Ala

<400> SEQUENCE: 5

```
Tyr Ser Phe Lys Pro Met Pro Leu Ala Arg Lys Gln Gly Gly Phe Leu
1               5                   10                  15

Gly Leu
```

<210> SEQ ID NO 6
<211> LENGTH: 9
<212> TYPE: PRT
<213> ORGANISM: Artificial sequence
<220> FEATURE:
<223> OTHER INFORMATION: Synthetic sequence

<400> SEQUENCE: 6

```
Tyr Lys Gln Gly Gly Phe Leu Gly Leu
1               5
```

<210> SEQ ID NO 7
<211> LENGTH: 20
<212> TYPE: PRT
<213> ORGANISM: Artificial sequence
<220> FEATURE:
<223> OTHER INFORMATION: Synthetic sequence

<400> SEQUENCE: 7

```
Gly Val Thr Ser Ala Pro Asp Thr Arg Arg Ala Pro Gly Ser Thr Ala
1               5                   10                  15

Pro Pro Ala His
            20
```

<210> SEQ ID NO 8
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (11)..(11)
<223> OTHER INFORMATION: Ala is d-Ala
<220> FEATURE:
<221> NAME/KEY: MISC_FEATURE
<222> LOCATION: (2)..(2)
<223> OTHER INFORMATION: Xaa is Ahx

<400> SEQUENCE: 8

```
Lys Xaa Tyr Ser Phe Lys Pro Met Pro Leu Ala Arg
1               5                   10
```

<210> SEQ ID NO 9
<211> LENGTH: 20
<212> TYPE: PRT
<213> ORGANISM: Artificial sequence
<220> FEATURE:
<223> OTHER INFORMATION: Synthetic sequence

<400> SEQUENCE: 9

```
Phe Pro Gly Trp Ala Glu Pro Asp Ser Asn Gly Ser Ala Gly Ser Glu
1               5                   10                  15

Asp Ala Gln Leu
            20
```

<210> SEQ ID NO 10
<211> LENGTH: 29
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (28)..(28)
<223> OTHER INFORMATION: Ala is d-Ala

<400> SEQUENCE: 10

```
Phe Pro Gly Trp Ala Glu Pro Asp Ser Asn Gly Ser Ala Gly Ser Glu
1               5                   10                  15

Asp Ala Gln Leu Tyr Ser Phe Lys Pro Met Leu Ala Arg
            20                  25
```

<210> SEQ ID NO 11
<211> LENGTH: 19
<212> TYPE: PRT
<213> ORGANISM: Artificial sequence
<220> FEATURE:
<223> OTHER INFORMATION: Synthetic sequence

<400> SEQUENCE: 11

```
Gly Asp Leu Ser Asp Pro Cys Gly Asn Arg Thr Asn Leu Gly Gly Arg
1               5                   10                  15

Asp Ser Leu
```

<210> SEQ ID NO 12
<211> LENGTH: 12
<212> TYPE: PRT
<213> ORGANISM: Artificial sequence
<220> FEATURE:
<223> OTHER INFORMATION: Synthetic sequence

<400> SEQUENCE: 12

```
Ile Pro Gln Ser Leu Asp Ser Trp Trp Thr Ser Leu
1               5                   10
```

<210> SEQ ID NO 13
<211> LENGTH: 22
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT -continued

```
<222> LOCATION: (21)..(21)
<223> OTHER INFORMATION: Ala is d-Ala

<400> SEQUENCE: 13

Ile Pro Gln Ser Leu Asp Ser Trp Trp Thr Ser Leu Tyr Ser Phe Lys
1               5                   10                  15

Pro Met Pro Leu Ala Arg
            20


<210> SEQ ID NO 14
<211> LENGTH: 24
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (23)..(23)
<223> OTHER INFORMATION: Ala is d-Ala

<400> SEQUENCE: 14

Ile Pro Gln Ser Leu Asp Ser Trp Trp Thr Ser Leu Arg Arg Tyr Ser
1               5                   10                  15

Phe Lys Pro Met Pro Leu Ala Arg
            20


<210> SEQ ID NO 15
<211> LENGTH: 26
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (25)..(25)
<223> OTHER INFORMATION: Ala is d-Ala

<400> SEQUENCE: 15

Ile Pro Gln Ser Leu Asp Ser Trp Trp Thr Ser Leu Arg Val Arg Arg
1               5                   10                  15

Tyr Ser Phe Lys Pro Met Pro Leu Ala Arg
            20                  25


<210> SEQ ID NO 16
<211> LENGTH: 24
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (9)..(9)
<223> OTHER INFORMATION: Ala is d-Ala

<400> SEQUENCE: 16

Tyr Ser Phe Lys Pro Met Pro Leu Ala Arg Arg Arg Ile Pro Gln Ser
1               5                   10                  15

Leu Asp Ser Trp Trp Thr Ser Leu
            20


<210> SEQ ID NO 17
<211> LENGTH: 25
<212> TYPE: PRT
<213> ORGANISM: Artificial sequence
<220> FEATURE:
<223> OTHER INFORMATION: Synthetic sequence
<220> FEATURE:
```

-continued

```
<221> NAME/KEY: VARIANT
<222> LOCATION: (23)..(23)
<223> OTHER INFORMATION: Ala is d-Ala

<400> SEQUENCE: 17

Ile Pro Gln Ser Leu Asp Ser Trp Trp Thr Ser Leu Arg Arg Tyr Ser
1               5                   10                  15

Phe Lys Pro Met Pro Leu Ala Arg Gly
            20                  25


<210> SEQ ID NO 18
<211> LENGTH: 14
<212> TYPE: PRT
<213> ORGANISM: Artificial sequence
<220> FEATURE:
<223> OTHER INFORMATION: Synthetic sequence

<400> SEQUENCE: 18

Ile Pro Gln Ser Leu Asp Ser Trp Trp Thr Ser Leu Arg Arg
1               5                   10


<210> SEQ ID NO 19
<211> LENGTH: 4
<212> TYPE: PRT
<213> ORGANISM: Artificial sequence
<220> FEATURE:
<223> OTHER INFORMATION: Synthetic sequence

<400> SEQUENCE: 19

Arg Val Arg Arg
1


<210> SEQ ID NO 20
<211> LENGTH: 4
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is K/R

<400> SEQUENCE: 20

Arg Xaa Xaa Arg
1
```

COMPOSITIONS AND METHODS FOR ENHANCING IMMUNE RESPONSES MEDIATED BY ANTIGEN-PRESENTING CELLS

This application is a continuation-in-part of U.S. application Ser. No. 09/051,685, filed Apr. 19, 1998, claiming priority to PCT US96/16825, filed Oct. 18, 1996 and U.S. Provisional Application No. 60/005,727, filed Oct. 20, 1995.

Pursuant to 35 U.S.C. §202(c), it is hereby acknowledged that the U.S. Government has certain rights in the invention described herein, which was made, in part, with funds from the National Institutes of Health, grant numbers CA 57362 and CA 36727.

FIELD OF THE INVENTION

The present invention relates to the field of vaccines and stimulation of acquired immunity. In particular, the present invention provides novel compositions designed to deliver specific antigens to antigen presenting cells and simultaneously deliver signals to those cells that produce a desired immune response.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

The basis of acquired, specific immunity in an organism is the ability to discriminate between self and non-self antigenic substances. The mammalian immune system uses cell surface molecules known as the major histocompatibility complex (MHC) for discriminating between self from non-self. There are two classes of MHC molecules: Class I molecules are found on all nucleated cell types in the body; Class II molecules are found mainly on cells involved in producing immune responses. Most specific immune responses are generated against peptides or peptide derivatives associated with MHC molecules.

The structure of MHC molecules is such that they naturally bind small peptides, glycopeptides, phosphopeptides, and the like. One important function of MHC molecules is to bind peptides that are derived from processed products of proteins expressed in cells expressing the MHC molecules, and to transport these to the cell surface for display to the immune system. In this way, some MHC molecules function to expose the immune system to peptides that are representative of normal cellular proteins. This process occurs during development, when self is learned, and continues throughout the organism's lifespan. Different mechanisms of immune tolerance prevent the organism from responding to "self" peptides associated with MHC.

The introduction of non-self proteins into cells results in the appearance of new and different peptides in association with the MHC molecules; these are recognized as "non-self," resulting in an immune response. For example, viral infection of a cell will result in the production of viral peptides expressed on the surface of antigen-presenting cells in association with MHC molecules (generally Class I MHC). Viral peptides presented with MHC molecules at the cell surface will often be recognized as foreign and an immune response will be mounted. Autoimmune disease can occur if tolerance to some self peptides is lost, or if immune response is produced against viral or other foreign proteins that cross react with normal peptides in the host organism.

In the case of bacterial infections or other insults from external sources, new proteins or compounds enter the organism. Some cells involved in the immune response are capable of phagocytosing foreign organisms or proteins. These immune cells degrade (process) the protein products and the derived peptides are expressed at the cell surface in association with MHC molecules, where a specific adaptive immune response is generated against novel non-self components. This activity is called antigen processing and presentation and cells that mediate this activity are called Antigen Presenting Cells (APC's). Many different immune cell types, including macrophages, dendritic cells, B cells, and other associated cell types, perform this function.

Antigen alone is often insufficient to produce an immune response. Sometimes, antigen must be presented with accompanying "signals" that are mediated by ligand-receptor interactions between the APCs and the responding lymphocytes or between these cells and soluble factors that are present in the surrounding environment. The soluble factors include cytokines and other mediators of inflammation that are usually present at sites of infections or insult (complement, kinins, other growth and cytokine factors). The signals can be positive in nature, resulting in lymphocyte proliferation and generation of an adaptive immune response, or negative in nature, resulting in apoptosis of responding lymphocytes and perhaps immune tolerance to that antigen. Antigen presentation often occurs in the presence of helper T cells or other cell types that secrete arrays of cytokines, which influence or determine the type of immune response that is induced. At a cellular level, specific immune responses are generated in a mixed cellular environment that includes different types of antigen presenting cells, helper T lymphocytes, other types of regulatory cells, and the responding lymphocytes (B cells for antibody responses and T cells for cellular responses). Direct recognition of peptides by T cells can also occur with some cell types, such as allografts, where the allogeneic MHC is directly recognized as foreign.

Antigen processing and its impact on types of immune responses to specific antigens. The mechanism by which antigen is processed and presented and the parameters that determine the types of immune responses that are generated (antibody versus cellular) are at present not well understood for many antigens. It is believed that there are different classes of APCs that can produce different types of immune responses. In general, APC-induced responses to exogenous antigens that are taken up by endocytosis are believed to be presented to the immune system in the context of Class II MHC and lead to recruitment of T helper cells that interact with B cells and ultimately produce an antibody response. In contrast, endogenous peptides from cells associate with MHC Class I molecules and produce cellular activities that include cytotoxic T lymphocytes (CTL) and Delayed Type Hypersensitivity (DTH) T-cells. There are important exceptions to these mechanisms. For example, many CTLs reactive with exogenous peptides have been described, and it is possible to generate CTLs to specific peptides that have been added to in vitro cultures of immune cells.

Other factors can determine the types of immune responses that are generated. For example, the nature of peptide association with MHC (either Class I or Class II) is an important factor that influences types of immune responses. In the case of Class I MHC molecules, there are specific binding motifs for peptide association (Rammensee et al, Ann. Rev. Imm. 11: 213, 1993). Binding motifs have been established for H-2 $K^d$, $K^k$, $D^d$, and other murine and human MHC. There are also parameters of peptide sequence that determine affinity for class II MHC. Thus, the types of peptides to which an individual can mount an immune system response are in part determined by the immunogenetic genotype and phenotype, which establish the shape and structure of the MHC molecules expressed by that individual.

In summary, the types of immune response that are generated in an organism in response to antigenic challenge is the result of a myriad of contributing factors, including: the immunogenetic background of the individual, prior sensitization to antigens, the route and form of antigen exposure, age and gender of the organism, and other factors. Almost all acquired immune responses that involve specific T-cell recognition are directed toward small peptides bound to the peptide binding groove of MHC molecules, the obvious exception being the response to superantigens. Cellular immune reaction (T-helper reaction, CTL, DTH) to peptides bound to MHC are usually generated through presentation of the antigen to T cells by antigen-presenting cells (APCs).

Tumor Vaccines. Cancer cells express aberrant molecules known as tumor-associated antigens. The immune system has the potential to recognize such structures as "foreign" and to mount specific immune responses against them, so as to reject tumor cells in much the same way that an allograft is rejected. This provides the basis for interest in the development of active specific immunotherapeutic (ASI) agents (cancer "vaccines") based on cancer-associated antigens.

Early studies on rodent tumors induced by chemical carcinogens, ultraviolet radiation, or viruses showed induction of immunological rejection of secondary tumor challenge. Subsequent studies on spontaneous tumors showed that these animals were incapable of inducing immune-mediated rejection of the tumor. Although a large number of human tumor-associated antigens have been characterized, most of these are also expressed by some normal cells. Therefore, immunological tolerance to such molecules makes it difficult to stimulate responses against such antigens. Moreover, it is a concern that induction of strong immune responses against self molecules may result in the development of autoimmune disorders. Since tumor-specific antigens are seldom detected in spontaneous cancers, approaches to develop active specific immunotherapy for common cancers, based on tumor-associated antigens, have been viewed with pessimism.

Nonetheless, interest in tumor immunology and the development of ASI in particular has persisted. There are at least four reasons for the current interest in ASI approaches. First, cell-mediated immune responses have been recognized as the key factor in immunological rejection of cancer. T cells recognize processed peptides in association with major histocompatibility complex (MHC) molecules, so intracellular proteins can give rise to peptide targets for cell-mediated responses. Further, since antigen processing and presentation are critical steps in T cell recognition, cancer-associated alterations (in its post-translational processing or levels of expression) of a self protein may result in presentation of novel peptide fragments on cancer cells. Secondly, tumor specific point mutations in certain genes have been characterized in several animal and human cancers. Some of these mutations generate novel peptide fragments that bind MHC molecules resulting in the production of new epitopes for recognition by T cells. This process allows for the induction of specific immune responses against cancer cells carrying such mutations. Third, manipulation of immune responses using cytokines, mutated antigens, and other means have sometimes resulted in tumor rejection even in cases of tumors that express weakly immunogenic antigens. Fourth, some individuals with severe immunodeficiencies have a higher incidence of tumors than the normal population, suggesting that the immune system plays an important role in eliminating some tumors.

Various methods have been utilized for stimulating general immune responses, especially for non-antigenic or weakly antigenic substances of interest. For example, adjuvants, such as complete Freund's and Ribi's, have long been used for this purpose. These adjuvants comprise oily solutions containing components, such as lipopolysaccharides that stimulate generalized immune responses. It is believed that the oils surround a water-soluble antigen, such as a peptide, thereby protecting it from degradation in the body and facilitating phagocytosis and passage through cell membranes of antigen presenting cells.

Another approach to stimulating the immunogenicity of a weakly-antigenic peptide or protein has been to couple the weak antigen to a carrier protein that is known to be a good immunogen. Common carrier proteins include keyhole limpet hemocyanin, fowl gamma-globulin and bovine serum albumin. Alternatively, the immunogencity of a weak antigen may be enhanced by polymerizing it into large aggregates by way of cross-linking agents, such as glutaraldehyde. Both these methods rest on the notion that a weak antigen coupled to a strong antigen will enhance the generalized immune response. In a similar method, solid-phase resins and peptide synthetic methods may be employed to synthesize a peptide repeatedly, to form a highly-branched complex. Again, the basis for this approach is to present the antigen in very unusual (and very "non-self") context to the immune system, to stimulate antibody production.

In yet another approach, a weakly antigenic protein or peptide is attached to a solid particle such as a latex bead or resin. The purpose of this approach is to enhance phagocytosis of the antigen by macrophages. Additionally, peptides and proteins have been encapsulated in liposomes to enhance passage through membranes of antigen presenting cells, to enhance phagocytosis and to stimulate generalized immune responses because of the "non-self" characteristics of the liposome carrier.

The approaches described above have met with varying degrees of success in stimulating the immunogenicity of weakly antigenic or non-antigenic substances. However, they provide only a generalized stimulation of immunity, and are not designed to target specific populations of immune system cells (such as antigen presenting cells). A desired objective in effecting therapeutic internvention in various disease states is to provide a means for specifically targeting a protein or peptide to a population of antigen-presenting cells and thereby stimulate those cells to internalize the antigen of interest and present it to the immune system in an effective, specific context. Insofar as it is known, such a system is not currently available.

SUMMARY OF THE INVENTION

The present invention provides novel compositions and methods for delivering specific antigens to antigen-presenting cells, and simultaneously delivering signals to those cells that produce a desired immune response. The compositions of the invention are sometimes referred to herein as "molecular adjuvants" or "APC-targeted activating antigens."

According to one aspect of the invention, these molecular adjuvants, which elicit an immune response mediated by an antigen-presenting cell, comprise at least one antigenic moiety (also referred to as an "immunogen") linked to at least one targeting moiety that binds specifically to a characteristic determinant on the antigen-presenting cell. For purposes of the present invention, the term "linked" is defined generally as physically linking of the moieties in such a way that each moiety retains its intended function. This is particularly relevant with respect to the targeting moiety, which is designed to bind to a characteristic determinant on the antigen-presenting cell.

In a preferred embodiment, the antigenic moiety is linked to the targeting moiety by a cleavable linker, such as a protease-sensitive dipeptide or oligopeptide. In one embodiment, the cleavable linker is sensitive to cleavage by a protease of the trypsin family of proteases. In another embodiment, the cleavable linker comprises a dibasic dipeptide sequence, such as an Arg-Arg dipeptide sequence or the tetrapeptide Arg-Val-Arg-Arg (SEQ ID NO:19).

Antigen-presenting cells contemplated for targeting according to the present invention include, but are not limited to, monocytes, dendritic cells, macrophages, B cells and some T cells. In preferred embodiments of the invention, the characteristic determinant on the selected APC is a cell surface receptor and the targeting moiety of the APC-targeted antigen is a ligand that binds to the receptor. It is particularly preferred that the cell surface receptor be an immunomodulatory receptor. Suitable cell surface receptors include, but are not limited to, C5a receptor, IFNγ receptor, CD21 (C3d) receptor, CD64 (FcγRI) receptor, and CD23 (FcεRII) receptor.

One exemplary APC-targeted antigen of the invention is designed to bind to the C5a receptor, and the targeting moiety is a C5a receptor ligand, which is preferably a peptide analog of C5a corresponding to the C-terminal 10 residues of C5a. Another exemplary composition of the present invention is designed to bind to the IFNγ receptor, and comprises a targeting moiety which is a IFNγ receptor ligand, preferably a peptide analog of IFNγ corresponding to the N-terminal 39 residues of IFNγ.

The antigenic moiety of the APC-targeted antigens of the invention can comprise essentially any antigenic substance, including, but not limited to, peptides and proteins, glycopeptides and glycoproteins, phosphopeptides and phosphoproteins, lipopeptides and lipoproteins, carbohydrates, nucleic acids and lipids. The APC-targeted antigens can comprise more than one antigenic moiety, and likewise can comprise more than one targeting moiety. Moreover, these moieties can be linked in several fashions. For instance, if "T" represents a targeting moiety, and "Ag" represents an antigenic moiety, the APC-targeted antigens of the present invention may be oriented as follows:

Ag-T;

T-Ag;

$T_1$-Ag-$T_2$;

$T_1$-$[Ag]_n$-$T_2$ (wherein $[Ag]_n$ represents a multiplicity of antigens.

Examples of the general formulas set forth above include:

Ag-C5a agonist peptide;

IFNγ peptide-Ag;

IFNγ peptide-$[Ag]_n$-C5a agonist peptide.

According to other aspects of the present invention, methods are provided for using the APC-targeted antigens of the invention. These include methods of activating an antigen-presenting cell with a targeting ligand and methods of eliciting an antigen presenting cell-mediated immune response in a subject in which such a response is desired. General methods of immunizing or vaccinating a patient requiring such treatment, methods of treating a tumor, and methods for producing antibodies specific for a pre-determined antigen for use as research tools or for diagnostic purposes are also contemplated to be within the scope of the present invention.

The numerous features and advantages of the compositions and methods of the present invention are described more fully in the detailed description set forth below.

BRIEF DESCRIPTION OF THE DRAWINGS

FIG. 6 is a graph showing that HBsAg-specific CTL responses are induced only by the C5a-active, protease-sensitive-linked constructs. BALB/c mice received three s.c. injections at 21 day intervals using 50 μg doses of the C5a-active constructs in which the HBsAg-$L^d$ MHC class I restricted peptide ($S_{28-39}$) was covalently attached directly to the N-terminus of the C5a agonist (IPQSLDSWWTSLYSFKPMPLaR; SEQ ID NO:13), spaced by two Arg residues (IPQSLDSWWTSLRRYSFKPMPLaR; SEQ ID NO:14), or spaced by the furin protease-sensitive sequence RVRR (SEQ ID NO:19) (IPQSLDSWWTSLRVRRYSFKPMPLaR; SEQ ID NO:15). Spleen cell suspensions were prepared from two mice in each group 14 days following the third injection. The cell suspensions were cultured in the presence of the $S_{28-39}$ peptide (75 nM) for four days and used as effector cells in $^{51}$Cr-release assays against P815S or P815 targets. Percent specific lysis of $^{51}$Cr-labeled P815S is shown and represent the means of triplicate determinations. Lysis of $^{51}$Cr-labeled P815 cells by these effector cells was less than 5% at an effector-to-target ratio of 50:1 (not shown).

DETAILED DESCRIPTION OF THE INVENTION

Figure 1:
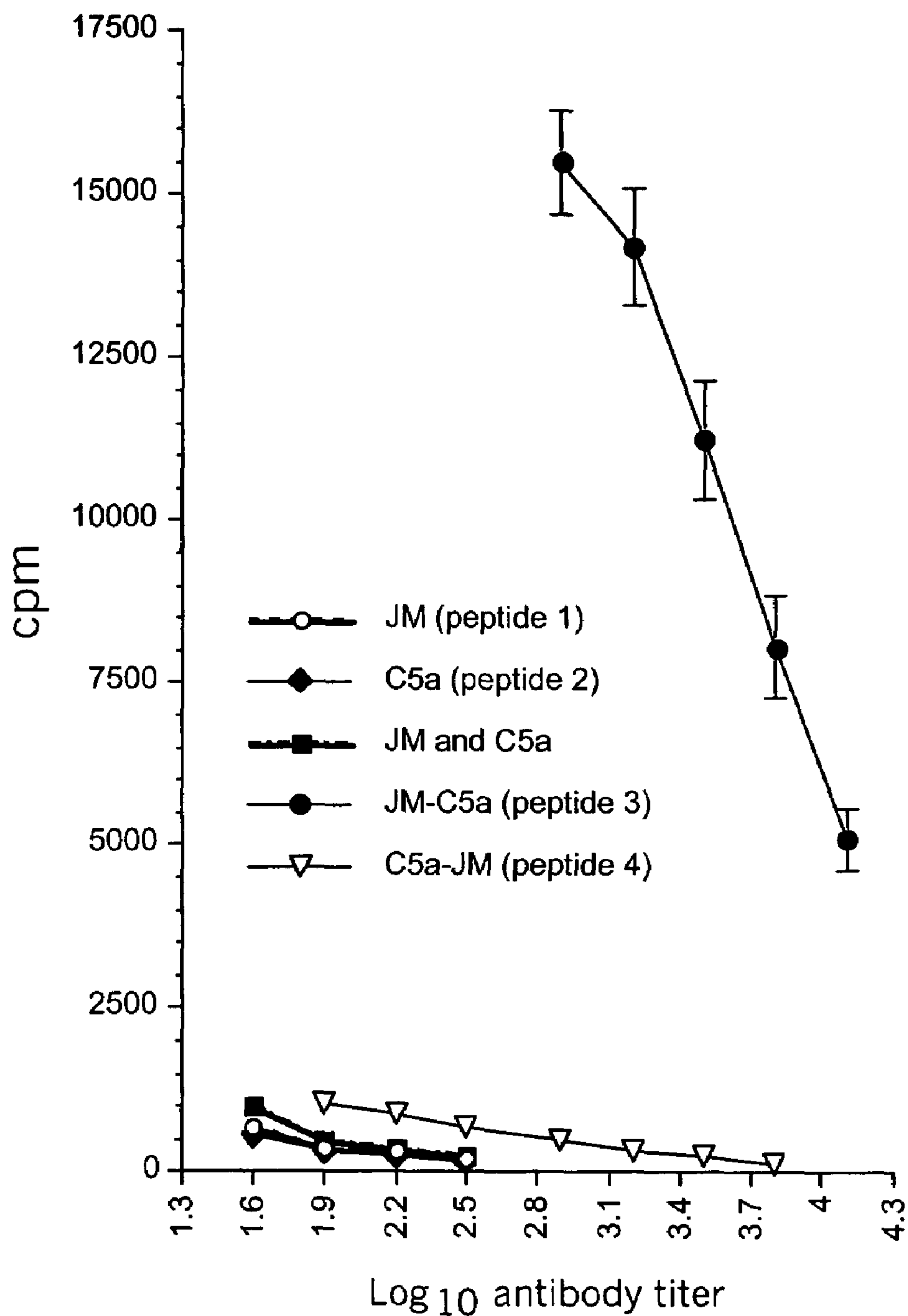
FIG. 1 is a graph illustrating the antibody titer produced in mice immunized with the indicated peptide constructs, as determined by radioimmunoassay, and shows the relationship between the amount of $^{125}$I-goat anti-mouse antibody bound vs. the dilution factor of mouse sera which had been incubated in microtiter wells coated with the MUC1 epitope peptide.

A major obstacle in the development of vaccines and other immunostimulatory agents is the inability of some antigens to be readily taken up and processed by antigen presenting cells. Uptake of antigens by APCs is an essential step for stimulating an effective immune response, since the immune system recognizes the antigen only after it has been processed by the APC and presented on the surface of the APC in conjunction with the major histocompatibility complex (MHC).

It is known that APCs, including dendritic cells, monocytes, macrophages and B cells, possess functional receptors for numerous molecules that modulate the immune response. It has now been discovered in accordance with the present invention that ligands which bind to these receptors can be conjugated to weakly immunogenic antigens for example, as a way of delivering antigens to the antigen presenting pathway of the APC and simultaneously activating the antigen presenting capacity of the APC. Thus, these conjugates bind to a receptor on the APC surface, transduce a biological signal, and are internalized by the APC. The antigenic moiety of the conjugate is thereby delivered to the antigen presenting pathway of the APC along with the simultaneous activation of the APC.

The above-described conjugates are sometimes referred to herein as "molecular adjuvants" or "APC-targeted activating antigens." The APC-targeted activating antigens of the invention are designed to elicit immune responses mediated by one or more types of antigen presenting cells. Accordingly, an APC-targeted activating antigen comprises at least one antigenic moiety physically linked to a targeting and activating moiety that binds specifically to at least one characteristic determinant on the selected antigen presenting cell type. This binding is followed by internalization of the APC-targeted antigen and results in presentation of the antigen moiety on the surface of the APC. For purposes of the present invention, the term "antigenic moiety" may refer to any substance to which it is desired that an immune response be produced. The selected antigenic moiety may or may not be capable of eliciting an immune response by conventional means.

The term "determinant" is used herein in its broad sense to denote an element that identifies or determines the nature of something. When used in reference to an antigen presenting cell, "determinant" means that site on the antigen presenting cell which is involved in specific binding by the targeting ligand moiety of the molecular adjuvant of the invention.

The expression "characteristic determinant" as used herein, signifies an epitope (or group of epitopes) that serves to identify a particular population of antigen presenting cells and distinguish it from other antigen presenting cell populations. Cell-associated determinants include, for example, components of the cell membrane, such as membrane-bound proteins or glycoproteins, including cell surface antigens, histo-compatibility antigens or membrane receptors.

The expression "specific binding", as used herein refers to the interaction between the targeting ligand moiety and a characteristic determinant on the antigen presenting cell population sought to be activated in accordance with this invention, to the substantial exclusion of determinants present on other cells.

Certain exemplary compositions of the invention have been synthesized, and have been shown to elicit APC-mediated immune responses in accordance with the mechanisms described above. For example, antigenic epitopes have been conjugated to the amino-terminal end of a C5a decapeptide agonist capable of binding to C5a receptors present on the surface of many APCs. Mice that were inoculated with an epitope of human MUC1 (a cell surface-associated mucin) conjugated to such a C5a agonist exhibited pronounced antibody titers against the MUC1 epitope, including high titers of specific antibodies with isotypes IgG2a and IgG2b. Mice that were inoculated with (1) MUC1 epitope alone, (2) C5a agonist alone, (3) unconjugated MUC1 epitope and C5a agonist together, or (4) C5a agonist conjugated to MUC1 epitope in a manner in which the biological activity of the C5a moiety was blocked, did not express a significant specific immune response. These results are described in greater detail in Example 1. Similar results were observed with conjugates of C5a agonist to a 12 kDa polypeptide, serum amyloid A (SAA), as described in greater detail in Example 2. These data tend to demonstrate the feasibility of the invention, which is to use receptor-binding ligands as a way to deliver antigens to APCs, with the simultaneous activation of APCs by the ligand moiety.

As described in greater detail below, the C5a receptor is only one of many receptors expressed on APCs. This invention encompasses the use of various ligands with selectivity to other receptors that mediate signal transduction events in the APCs, to be used alone or in conjunction with C5a agonists to influence the nature of immune response generated, i.e., humoral, cellular, Th1, Th2, and the like. Vaccines and other immunotherapeutic agents can be prepared with an array of such targeting moieties that serve to target the antigen moiety to a specific population of APCs and simultaneously activate these and other cells involved in various immune modulatory pathways.

The detailed description below sets forth preferred embodiments for making and using the targeted antigens of the present invention. To the extent that specific compounds and reagents are mentioned, these are for the purposes of illustration, and are not intended to limit the invention. Any biochemical, molecular or recombinant DNA techniques not specifically described are carried out by standard methods, as generally set forth for example, in Ausubel et al., "Current Protocols in Molecular Biology," John Wiley & Sons, Inc., 2000.

I. Preparing APC-Targeted Activating Antigens

A. Selection of Components

Antigen presenting cells have various receptors on their surfaces for known ligands. Binding of ligands to these receptors results in signal transduction events that stimulate immune or tolerance responses. Many of these receptors are known to internalize and recycle in the cell. Others are suspected of doing the same. As such, these receptors are ideal targets for delivering antigens and activation signals simultaneously to APCs.

As discussed above, APCs include several cell types including macrophages, monocytes, dendritic cells, B cells, some T cells and other poorly characterized cell types. It is believed that these different classes of APCs can produce different types of immune responses. Accordingly, by targeting a receptor prevalent on a specific population of APCs, a particular desired immune response may be favored. An exemplary list of receptors contemplated for targeting in the present invention, and the rationale for their selection, is set forth below. These APC receptors are particularly appropriate for use in the present invention based on the following criteria: they are receptors expressed on APCs; the receptors are internalized upon binding of ligand; the receptors can transmit signals in the cells that influence antigen processing and presentation by these cells; some of the receptors are believed to be involved in signaling Th1 type cellular responses, whereas others are predicted to generate Th2 type humoral responses. The list set forth below is not exhaustive, but merely representative of the type of targeted receptors preferred in practicing the present invention. Other receptors, or other cell-surface characteristic determinants on antigen presenting cells may also be used as targets for the targeted antigens of the present invention. The receptor or other characteristic determinant need not be directly involved in the immune response.

C5a receptor. This receptor is preferred for use according to the present invention. It is present on PMNs, macrophages, dendritic cells, smooth muscle cells and some mast cells. A number of biological activities have been ascribed to C5a, mostly associated with inflammatory and immune responses. According to a preferred embodiment, this invention relies on the capability of C5a, as a targeting ligand, to specifically bind to its cognate receptor, so as to activate antigen presenting cells, including macrophages, monocytes and dendritic cells, through a G protein-mediated signal transduction pathway. Subsequent to signal transduction, the receptor/ligand complex is internalized. In the case of dendritic cells, C5a has been shown to induce a Th1 type response.

IFNγ receptor. The interferon γ receptor is expressed on macrophages, monocytes, dendritic cells, other APCs, some B cells, fibroblasts, epithelial cells, endothelium, and colon carcinoma cells. IFNγ binding to its receptor induces macrophage and dendritic cell activation, B cell differentiation, and expression of MHC class I and class II molecules in many cell types. The receptor is involved in signal transduction pathways. IFNγ is mainly produced in the body by activated T cells, particularly during the generation of Th1 type response. It is also produced by CD8+ cytotoxic T lymphocytes following recognition of antigen associated with MHC class I and by natural killer cells stimulated with TNFα and microbial products (Barclay et al. 1993).

CD 21 (C3d receptor). CD 21 is the receptor for the C3d complement fragment. It is a receptor for the Epstein-Barr virus and may be an important interferon α receptor (Barclay et al., supra). CD 21 is expressed on B cells, follicular dendritic cells, other APCs, pharyngeal and cervical epithelial cells, and some thymocytes. It is involved in activation and proliferation of B cells through a signal transduction mechanism and it has been associated with increases in antigen presentation activities by those cells.

CD 64 (FcγRI receptor). CD 64 is a high affinity receptor for IgG, the only known receptor that binds monomeric IgG (Barclay et al, supra). This receptor is found on macrophages, monocytes and other immune cell populations treated with IFNγ. The $IgG_1$ binding site resides in the CH2 domain. IFNγ strongly upregulates expression of this receptor, which is the primary receptor involved in antibody-dependent cell mediated cytotoxicity reaction, and phagocytic activity by these cells.

CD 23 (FcεRII receptor). CD 23 is a low affinity receptor for IgE (not related to the high affinity IgE receptor found on basophils and mast cells). It is found on some B cell populations, macrophages, eosinophils, platelets, and dendritic cells (Barclay et al, supra). CD 23 mediates IgE dependent cell mediated cytotoxicity and phagocytosis by macrophages and eosinophils, and binding of IgE immunocomplexes increases the efficiency of antigen processing and presentation by some APCs, through a signal transduction mechanism that includes the p59 fyn tyrosine kinase. The ligand for CD 23 is the Cε3 domain of IgE.

As mentioned above, the APC-targeted antigens of the present invention comprise at least one antigenic moiety and at least one targeting moiety. The targeting moiety can be derived from naturally-occurring ligands for a selected receptor on an APC, or analogs and derivatives of such ligands. For instance, the C5a receptor is a preferred receptor for use in practicing the present invention. Naturally-occurring C5a can be utilized as the targeting moiety in the APC targeted activating antigens of the invention. However, native C5a is not preferred for use as the targeting moiety as it induces a myriad of pro-inflammatory responses which may have undesirable side effects. In particularly preferred embodiments of the invention, C-terminal C5a agonist analogs capable of C5a receptor binding and signal transduction in a response selective manner are utilized. Such analogs are described in detail in U.S. Pat. Nos. 5,696,230 and 5,942,599 to Sanderson et al., the entireties of which are incorporated by reference herein.

An exemplary C5a C-terminal decapeptide agonist preferred for use in the present invention is:

YSFKPMPLaR (SEQ ID NO:1)

This decapeptide is a potent agonist of naturally occurring C5a, and is preferred to naturally occurring C5a because its small size contributes to ease of synthesis and solubility. Moreover, these conformationally biased peptides are stable toward serum carboxypeptidase digestion, express a level biological selectivity, and have been shown to be non-toxic in high concentrations in athymic mice.

Peptide analogs of naturally-occurring interferon γ are also contemplated for use in the present invention. Peptides corresponding to the amino terminal 39 amino acids of IFNγ have been shown to compete for binding with native IFNγ. Antibodies against this domain block biological activity, and removal of the first 10 amino terminal residues eliminates biological activity. This suggests that binding of IFNγ to its cognate receptor is mediated by this portion of the molecule. Accordingly, peptides based on this domain are contemplated to be of use for delivering antigens to APCs expressing IFNγ receptors. In this regard, it should be noted that human and mouse IFNγ are absolutely species specific in binding and activity. Consequently, for stimulating APC-mediated immune responses in mice, the mouse peptides will be utilized, and the human peptide will likewise be utilized for stimulating APC-mediated immune responses in humans. The mouse IFNγ 39 amino acid peptide analog is composed of the following sequence: HGTVIESLESLNNYFNFFGIDVEEKSLFLDIWRNWQKDG (SEQ ID NO:3) The human IFNγ 39 amino acid peptide analog is composed of the following sequence: QDPYVKEAENLKKYFNAGHSDVADNGTLFLGILKNWKEE (SEQ ID NO:4)

Another ligand contemplated for use in the present invention is the C3dG component of complement. This component is a 348 residue fragment derived by proteolytic cleavage from the C3b precursor (residue 955–1303 of C3; Swissprot accession p01024). C3dG can be converted to C3d (residues 1002–1303) and C3g (residues 955–1001). C3dG and C3d remain associated with non-activator surfaces and serve as opsonins for phagocytosis by macrophages and other antigen presenting cells. Cd 21 is the C3dG and C3d receptor.

The above-listed ligands exemplify the type of ligand preferred for practice of the present invention. However, it will be appreciated by those skilled in the art that other ligands may be utilized as the targeting moiety of the APC-targeted antigens of the invention. These include ligands that are already known in the art, as well as ligands that may be discovered and developed henceforth. Antibodies or antibody fragments also may be used to target APC-specific cell surface antigens.

The type of antigen that can be chosen as the antigenic moiety in the present invention can be any peptide, polypeptide or derivative thereof for which an immune response or antibody production is desired. These include but are not limited to, peptides, polypeptides (i.e. proteins) and derivatives thereof, such as glycopeptides, phosphopeptides and the like. Synthetic peptide and polypeptide derivatives or analogs, or any other similar compound that can be conjugated to a receptor-targeting moiety can be used in the present invention. Moreover, these peptides, proteins and derivatives may comprise single epitopes or multiple epitopes for generating different types of immune responses. Indeed, if an entire protein is conjugated to a targeting moiety, this protein is likely to comprise numerous epitopes, which may vary depending upon the solvent conditions and their effect on secondary and tertiary structure of the protein. Carbohydrates, nucleic acids and other non-protein substances also may be used as the antigenic moiety. Methods are available in the art for conjugating these substances to the peptide or protein targeting moiety.

Other substances that can be used as the antigenic moiety include small molecules, such as (1) metabolic byproducts (especially those that are toxic); (2) various environmental toxins or irritants (e.g., aromatic hydrocarbons, asbestos, mercury compounds and the like); (3) drugs (e.g., cocaine, heroin, nicotine, etc.) for treating addiction; and (4) venoms from snakes, spiders or other organisms. Many of these kinds of small molecules are non-antigenic or weakly antigenic, so would be appropriate candidates for use in the present invention.

In preferred embodiments of the invention, the antigenic moiety comprises agents that are weakly antigenic or non-antigenic under currently available immunization conditions. Many tumor-associated antigens fall into this category, because the antigens also are expressed by normal cells. Therefore, immunological tolerance to such molecules makes it difficult to stimulate responses against such antigens. Other proteins that fall into this category include naturally occurring proteins from one species (e.g., human) for which it would be desirable to produce antibodies in another species but which are recalcitrant to antibody generation in the other species.

One well-characterized tumor antigen is a cell surface-associated mucin that is highly overexpressed and differentially glycosylated by different adenocarcinomas, including breast, pancreas, lung and prostate carcinomas. Aberrant glycosylation of MUC1 by adenocarcinomas results in the addition of some blood group carbohydrate antigens to this core protein and the exposure of epitopes which have been detected by monoclonal antibodies on the core protein that are not exposed on forms of this protein produced by normal epithelial cells. A full-length cDNA sequence of human mucin-1 (MUC1) revealed an encoded protein with an average length of approximately 1200 amino acids (depending on the length of the tandem repeat allele) with several obvious domains: an amino terminal signal peptide; a large domain made up of multiple identical 20 amino acid tandem repeats flanked by several repeats that contain degenerate sequences; a hydrophobic-spanning domain of 31 amino acids; and a cytoplasmic domain of 69 amino acids at the carboxyl terminus. The most well-characterized tumor associated epitopes described to date for MUC1 are found in the tandem repeat domain. These include carbohydrate structures and protein structures. MUC1 tumor associated epitopes are well characterized, and thus have been proposed to be used for the production of tumor vaccines using conventional methods. Exemplary compositions of the present invention comprise MUC1 epitopes, such as those set forth below, as the antigenic moiety of the APC-1 targeted antigens of the invention, to demonstrate the potential of the present invention as potent tumor vaccines.

MUC1 epitope predicted to bind to class I molecules of the H-2k$^{b}$ type has sequence homology to the juxtamembrane region of MUC1;

YKQGGFLGL (SEQ ID NO:6)

MUC1 tandem repeat has the sequence:

GVTSAPDTRRAPGSTAPPAH (SEQ ID NO:7)

The components comprising the APC-targeted antigens of the invention can be made separately, then conjugated. For example, a small peptide analog, such as the above-described C5a agonists, may be produced by peptide synthetic methods, and conjugated to a protein which has been purified from naturally occuring biological sources. Alternatively proteins engineered for expression via recombinant methods may be used. Additionally, targeted antigens comprising peptide components (i.e., a peptide antigenic epitope conjugated to a peptide receptor ligand) can be synthesized in tandem by peptide synthetic chemistry according to known methods and as described in greater detail below. Finally, targeted antigens of the invention comprising two larger polypeptide moieties (i.e., a large polypeptide antigen linked to a large ligand) can be made by recombinant techniques. For example, DNA molecules encoding both components can be ligated together by recombinant means, then expressed as the conjugated fusion protein. Methods of making these different types of compositions are set forth in greater detail below.

B. Peptides

Oligopeptides required for the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. When solid-phase synthesis is utilized, the C-terminal amino acid is linked to an insoluble resin support that can produce a detachable bond by reacting with a carboxyl group in a C-terminal amino acid. One preferred insoluble resin support is p-hydroxymethylphenoxymethyl polystyrene (HMP) resin. Other useful resins include, but are not limited to: phenylacetamidomethyl (PAM) resins for synthesis of some N-methyl-containing peptides (this resin is used with the Boc method of solid phase synthesis; and MBHA (p-methylbenzhydrylamine) resins for producing peptides having C-terminal amide groups.

During the course of peptide synthesis, branched chain amino and carboxyl groups may be protected/deprotected as needed, using commonly-known protecting groups. In a preferred embodiment, $N^{\alpha}$-amino groups are protected with the base-labile 9-fluorenylmethyloxycarbonyl (Fmoc) group or t-butyloxycarbonyl (Boc groups). Side-chain functional groups consistent with Fmoc synthesis may be protected with the indicated protecting groups as follows: arginine (2,2,5,7,8-pentamethylchroman-6-sulfonyl); asparagine (O-t-butyl ester); cysteine glutamine and histidine (trityl); lysine (t-butyloxycarbonyl); serine and tyrosine (t-butyl). Modification utilizing alternative protecting groups for peptides and peptide derivatives will be apparent to those of skill in the art.

C. Proteins

Full-length proteins for use in the present invention may be prepared in a variety of ways, according to known methods. Proteins may be purified from appropriate sources, e.g., human or animal cultured cells or tissues, by various methods such as gel filtration, ion exchange chromatography, reverse-phase HPLC and immunoaffinity purification, among others. However, due to the often limited amount of a protein present in a sample at any given time, conventional purification techniques are not preferred in the present invention.

The availability of nucleic acids molecules encoding a protein enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, a selected peptide or protein may be produced by expression in a suitable procaryotic or eucaryotic system. For example, a DNA molecule, encoding a peptide or protein component of the invention, or an entire composite targeted antigen of the invention, may be inserted into a plasmid vector adapted for expression in a bacterial cell, such as *E. coli*, or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

A peptide or protein produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, so as to be readily purified from the surrounding medium. If expression/secretion vectors are not used, an alternative approach involves purifying the recombinant protein by affinity separation, such as by immunological interaction with antibodies that bind specifically to the recombinant protein. Such methods are commonly used for isolating peptides and proteins.

D. Linking Separately-Made Proteins and/or Peptides

In an alternative embodiment, protein and/or peptide components of the invention are synthesized separately, then conjugated using standard methods known by those skilled in the art. For example, a synthetic peptide may be chemically coupled to a protein using m-maleimidobenzoyl-N-hydroxysuccinimide ester (MBF). This reagent cross-links amino- and carboxy-terminal thiol groups in the peptide with lysine side chains present in the protein. Alternatively, a synthetic peptide may be coupled to a protein using glutaraldehyde, a common cross-linking agent. Another method for chemically coupling a peptide to a protein is through the use of carbodiimide and 1-(3-dimethylamino-propyl)-3-ethylcarbodiimide methiodide (EDC). As described in greater detail in Example 2, this method was used to conjugate a C5a C-terminal decapeptide analog to serum amyloid A (SAA). Methods for joining two proteins together are also available.

The peptides or proteins of the invention, prepared by the aforementioned methods, may be analyzed according to standard procedures. For example, they may be subjected to amino acid sequence analysis, mass spectra analysis or amino acid compositional analysis according to known methods.

E. General Formulae and Exemplary Compositions of the Invention

The APC-targeted antigens of the invention can comprise one or more antigenic moieties, and likewise can comprise one or more targeting moieties. Moreover, these moieties can be linked in several ways. For instance, if "T" represents a targeting moiety, and "Ag" represents an antigenic moiety, the APC-targeted antigens of the present invention may be organized as follows:

Ag-T;

T-Ag;

$T_1$-Ag-$T_2$;

$T_1$-$[Ag]_n$-$T_2$ (wherein $[Ag]_n$ represents a multiplicity of antigens.

Examples of the general formulas set forth above include:

Ag-C5a agonist peptide;

IFNγ peptide-Ag;

IFNγ peptide-$[Ag]_n$-C5a agonist peptide.

Other representative compositions of the invention include:

MUC1 Class I binding epitope-C5a agonist C-terminal peptide

Murine or human IFNγ peptide-MUC1 Class I binding epitope

Murine or human IFNγ peptide-MUC1 tandem repeat

MUC1 Class I epitope—C3dG peptide

SAA-K-Ahx-C5a C-terminal peptide (Ahx=ϵamino hexanoic acid).

It will be appreciated by persons skilled in the art that the APC-targeted activating antigens of the invention may be adapted for inclusion of large or complex antigens. This may be accomplished, for example, by inclusion of a "spacer" (such as the K-Ahx spacer moiety in the exemplary compound above) between the antigen and the targeting moiety. Such chemical modifications are familiar to biochemists.

Cleavable linkers. In addition to the foregoing sorts of spacers and linkers, it has also been discovered in accordance with the present invention that introduction of a cleavage-prone oligopeptide between the targeting moiety and the antigen can improve the immunogenicity of the molecule. For instance, as described in greater detail in Example 5, an Arg-Arg dipeptide or an Arg-Val-Arg-Arg (SEQ ID NO:19) tetrapeptide between the C5a peptide analog, YSFKPMPLaR (SEQ ID NO:1) and a cytotoxic T lymphocyte (CTL) epitope of hepatitis B virus surface antigen was found to robustly elicit a CTL response to the antigen in mice, in the absence of added adjuvant. The Arg-Arg dipeptide adds a scissile bond that is susceptible to cleavage or cleavage by trypsin-like protease (e.g., subtilisin). The Arg-Val-Arg-Arg (SEQ ID NO:19) tetrapeptide imbues sensitivity to cleavage by furin (another trypsin-like protease). While not intending to be limited by any particular explanation of the underlying mechanism by which the robust CTL response was elicited, it is believed that the Arg-Arg or Arg-Val-Arg-Arg (SEQ ID NO:19) protease-sensitive linker peptides facilitate cleavage of the molecule adjuvant within the APC, thereby more expeditiously freeing the antigen for further processing and presentation on the APC cell surface.

Other scissile bond dipeptides or other oligopeptides also can be inserted between the targeting moiety and the antigen. These include residues to create a peptide bond(s) that is susceptible to other cytoplasmic proteases or proteases found within any of the intracellular antigen processing organelles. Preferred sites comprise dibasic dipeptides (i.e., various dipeptide permutations comprising Arg, Lys or His) or oligopeptide cleavage sites for the trypsin family of proteases.

Another option is the creation of a dipeptide scissile bond that is susceptible to acid-catalyzed hydrolysis when exposed to the acidic conditions typically found within intracellular endosomal/lysosomal compartments of an antigen presenting cell (APC). In addition, other epitope-targeting moiety linkages are contemplated to have a similar utility in the efficiency of processing by APCs. These include sequences that are known or suspected to facilitate or enhance 1) the transport/uptake of epitope constructs into the rough endoplasmic reticulum (RER), 2) the association of epitope to MHC class I and/or class II determinants, 3) transport of epitope through the cis, medial, and trans Golgi apparati, and 4) entry into transport vehicles associated with MHC class I."

Thus, a variety of "cleavable linkers" can be inserted between the targeting moiety and the antigen to facilitate processing of the antigen by the antigen-presenting cells. As used herein, the term "cleavable linker" refers to any linker between the antigenic moiety and the targeting moiety that promotes or otherwise renders the molecular adjuvant more susceptible to cleavage (by proteases, low pH or any other means that may occur within or around the antigen-presenting cell) and, thereby, processing by the antigen-presenting cell, than an equivalent molecular adjuvant lacking such a cleavable linker.

II. Uses of APC-Targeted Activating Antigens

The APC-targeted activating antigens of the present invention have broad potential for clinical applications in humans and animals. As discussed above, a significant impediment to the development of vaccines and other immunotherapeutic agents is the apparent inability of particular antigens to be readily taken up and processed by antigen presenting cells. The compositions of the invention faciliate the specific delivery of an antigen to a population of antigen presenting cells, whereupon the delivery mechanism (e.g., using as the targeting moiety a receptor ligand capable of transducing a biological signal) simultaneously activates the antigen presenting pathway of the APC. Thus, the present invention enables development of vaccines and other immunotherapeutics that can specifically target any peptide antigen or other antigenic structure covalently attached to a ligand for a receptor present on an antigen presenting cell. It is believed that antigens linked to ligands that selectivity bind to and activate a particular population of APCs can not only generate an immune response, but can influence the nature of the immune response that is generated. Thus, immune responses that favor antibody, cellular, Th1 or Th2 responses, respectively, may be selectively generated. Vaccines may also be developed with an array of such targeting moieties thereby serving to target a selected antigen or antigens to several populations of APCs and simultaneously activate these and other cells involved in various immune modulatory pathways.

The ability to generate either antibody or cell mediated immune responses against different specific antigens has broad general applicability, and it is anticipated that the APC-targeted antigens of the invention will be extremely useful for these purposes. For example, antibody responses have been shown to be capable of protecting against different viral or bacterial infection, and antibodies are known to inactivate different toxins or toxic compounds that may affect the well being of humans or animals. Different cell mediated immune responses can provide protection against viral or other intracellular pathogens, and can play a role in some anti-tumor responses. It is believed that different antigen presenting cells and the context in which these cells are stimulated to present antigen (co-stimulation mediated by different ligand-receptor interactions) are important factors determining the nature of the above responses.

The targeted antigens of the present invention should find particular utility in the development of active specific immunotherapeutic agents (i.e., cancer "vaccines") based on cancer-associated antigens. For example, it has been hypothesized that induction of strong cell-mediated immune responses (involving Th1 cells and/or cytotoxic T lymphocytes) would provide the most effective protection against various forms of cancer. A vaccination strategy utilizing the APC-targeted antigens of the invention can be designed to induce this type of response. In this regard, it is known that stimulation with some cytokines (IL-12, IFNγ) can induce predominantly Th1 type responses over Th2 type responses for certain antigens.

As a step toward developing anti-cancer vaccines for clinical use, the compositions of the invention can be used to advantage as research tools to further explore the effect of stimulating a certain population of APCs with a tumor antigen and determining the effect on an anti-tumor immune response. To this end, it should be noted that the present application exemplifies targeted antigens comprising an epitope of a particular tumor-specific antigen, Mucin-1.

Previous tumor vaccine formulations that aim to immunize patients with compounds that are identical to compounds already produced by tumors have proven to be of limited value, probably because tumors that progress have been selected for their lack of immunogenicity in their respective host (e.g., the host is tolerant to existing tumor antigens). Thus, one important challenge of producing effective tumor vaccines is generating reagents that counteract immunological tolerance to tumor-associated antigens. One purpose of the APC-targeted antigens described above is to induce in the immunized individual a response against their tumor that is similar to that seen in individuals undergoing allograft rejection. In other words, the goal is to induce an autoimmune reaction against the tumor that is capable of destroying the tumor. The immunological parameters that regulate tolerance to tumor antigens are not well understood; nonetheless the compositions described herein have the potential to counteract this tolerance and thus induce specific immune responses that mediate tumor rejection.

The targeted antigens of the present invention will also find broad utility in the production of antibodies for use as immunodiagnostic and immunotherapeutic agents. For immundiagnostic purposes, antibodies are widely used in various quantitative and qualitative assays for the detection and measurement of biological molecules associated with diseases or other pathological conditions. For reasons that often are not well understood, it is sometimes difficult to generate antibodies against certain biological molecules using conventional means. The compositions of the present invention provide an alternative means for inducing an animal to produce antibodies against a weakly-antigenic or non-antigenic substances. The utility of the compositions of the invention in this regard is shown clearly in Example 2, below, in connection with serum amyloid A. The appearance and abundance of this protein in the body is strongly correlated with systemic inflammatory stress, which is a condition that is very difficult to quantitate. It is believed that quantitative assays for SAA levels would be an excellent indicator of general, systemic inflammation; thererfore it would be of benefit to generate antibodies against the protein in a non-human species. This protein has proved particularly recalcitrant to the generation of antibodies using conventional measures. As described in Example 2, a targeted antigen comprising SAA conjugated to a C5a peptide ligand produced a significant antibody response in mice injected with the conjugated molecule. In a similar fashion, targeted antigens comprising any weakly-antigenic or non-antigenic component of interest could be made and used to produce specific antibodies in laboratory animals, for use as immunodiagnostic reagents.

Antibodies for use as immunotherapeutic agents can also be generated using the compositions of the invention. As one example, there has been a great deal of recent interest in developing reagents capable of down-regulating or inhibiting the complement cascade to modulate local and systemic inflammatory responses. To this end, the C3a convertase, which is active early in the cascade, could provide an ideal target for complement inhibition. C3a convertase cleaves the peptide C3 into two components, C3a and C3b, and therefore must be able to access the cleavage site on C3 in order to accomplish the result. Antibodies directed toward the C3a-C3b cleavage site are expected to be effective in blocking access of C3a convertase to the cleavage site, thereby inhibiting this early step in the complement cascade. Such antibodies may be generated using a targeted antigen of the invention comprising, as the antigenic moiety, the short peptide sequence comprising the C3a/C3b cleavage site. The sequence could then be conjugated to an appropriate targeting moiety, such as the C5a C-terminal decapeptide agonists exemplified herein. Thus, the compositions would be useful to generate an immunotherapeutic agent (e.g., an antibody that blocks the activity of C3a convertase) for treating an adverse inflammatory condition.

The following examples are provided to describe the invention in further detail. These examples are intended to illustrate the invention in greater detail. They are not intended to limit the invention in any way.

EXAMPLE 1

Evaluation of Mucin Epitope (MUC1/C5a Agonist) Conjugate for Recruitment and Activation of Antigen Presenting Cells (APCs) and Stimulation of an Immune Response in Mice The C5a receptor is present on numerous antigen presenting cells, including monocytes, macrophages, dendritic cells, and other cell types. In this example, a composite peptide comprising a mucin epitope (MUC1) fuctionally linked to a decapetide agonist analog of C5a corresponding to the C-terminal effector region of the natural factor was evaluated for its ability to activate the APCs thereby stimulating an immune response in mice. This evaluation is based on the known property of C5a receptors to internalize and recycle in the antigen presenting cell, thereby acting as ideal candidates for delivering antigens to and simultaneously activating signals in the APCs. Because C5a receptors are particularly common on macrophages, monocytes and dendritic cells, it is believed that the use of a C5a agonist analog to bind C5a receptors will result in preferential activation of these APCs.

i. Abbreviations. Except where noted, the single letter designation for the amino acid residues is used: alanine is A; arginine is R; asparagine is N; aspartic acid is D; cystine is C; glutamine is Q; glutamic acid is E; glycine is G; histidine is H; isoleucine is I; leucine is L; lysine is K; methionine is M; phenylalanine is F; proline is P; serine is S; threonine is T; tryptophan is W; tyrosine is Y; and valine is V. Upper case letters represent the L-amino acid isomer and lower case the D-isomer.

ii. Peptide Synthesis, Purification and Characterization. The following peptides were synthesized according to standard solid-phase methodologies on an Applied Biosystems (Foster City, Calif.) model 430 A peptide synthesizer and characterized as previously described (7):

(1) The antigenic "juxta-membrane" (JM) epitope of the human mucin-1 (MUC1), YKQGGFLGL (SEQ ID NO:6);

(2) The C5a C-terminal decapeptide agonist analog, YSFKPMPLaR (SEQ ID NO:1);

(3) The composite peptide YKQGGFLGLYSFKPMPLaR (SEQ ID NO:2), in which the JM epitope is positioned toward the amino terminus and the C5a peptide is positioned toward the carboxyl terminus; and (4) The composite peptide YSFKPMPLaRKQGGFLGL (SEQ ID NO:5), in which the JM epitope of MUC1 is positioned toward the carboxyl terminus and the C5a analog is positioned toward the amino terminus.

Peptide 3 retains C5a biological activity, whereas peptide 4 does not because the biologically important carboxyl terminal end of the C5a analog is blocked by the presence of the mucin epitope. As such, peptide 4 serves as a control to determine the importance of the C5a biological activity to the effectiveness of these peptides for immunization purposes.

Syntheses were performed on a 0.25 mmol scale on 0-hydroxymethylphenoxymethyl polystyrene (HMP) resins (0.88 meq/g substitution). $N^{\alpha}$-amino groups were protected with the base-labile 9-fluorenylmethyloxycarbonyl (Fmoc) group. Side-chain functional groups were protected as follows: Arg (Pmc or 2,2,5,7,8-pentamethylchroman-6-sulfonyl); Asp (Ot-butyl ester); Cys, Gln & His (Trt or trityl); Lys (Boc or t-butyloxycarbonyl); Ser & Tyr (t-butyl). Synthesis was initiated by the in situ coupling of the C-terminal residue ($N^{\alpha}$-Fmoc-L-Arg(Pmc)) to the HMP resin in the presence of excess N-N'-dicyclohexylcarbodiimide (DCC) and 1-hydroxybenzotriazole (HOBT) with 4-dimethylaminopyridine (DMAP) as a coupling catalyst. Peptide chain elongation was accomplished by repetitive Fmoc deprotection in 50% piperidine in NMP followed by residue coupling in the presence of 2-(1H-benzotriazol-1-yl)-1,1,3,3-tetramethyluronium hexafluorophosphate (HBTU).

Side-chain deprotection and cleavage from the resin were achieved in a single step acetolysis reaction by stirring the peptide-resin in a solution of 84% trifluoroacetic acid (TFA), 6% phenol, 2% ethanedithiol, 4% thioanisole, and 4% water for 1.5 hr at room temperature. Free peptide was precipitated from this solution by adding cold diethyl ether. The mixture was filtered through a scintered glass Buchner funnel (medium porosity) and the peptide/resin washed twice with cold ether to remove the thiol scavenger. The peptide was extracted by swirling the peptide/resin in the funnel with 20–30 ml aliquots of 10% acetic acid followed by filtration. The extraction aliquots were combined, frozen, and lyophilized to yield the powdered form of the crude peptide.

Peptides were purified by preparative and analytical reverse-phase HPLC on columns packed with $C_{18}$-bonded silica. The details of this procedure have been described by (4). All peptides were characterized by amino acid compositional analysis and fast atom bombardment mass spectrometry (FAB-MS).

iii. Animal Models. The strains of mice used for this example were inbred females 6 to 12 week old C57B16(H-$2^b$) and Balb/c (H-$2^d$), which were obtained from Jackson labs (Bar Harbor, Me.). These two strains which differ in H-2 haplotypes, were used in this example to demonstrate that the observed antibody responses were not a result of the selection or creation of an unique immunogenic epitope characteristic of the sequence of the proteins of the MHC class I and class II molecules important for antigen processing in one mouse strain or another. The MUC1 peptide selected for these studies contained a motif that may bind to the H-2 $K^b$ molecule of the C57B16 mice; therefore, a strain of mouse that lacked this class I molecule binding motif (Balb/c) was also studied to determine the relative contribution of the class I binding motif to the antigen presentation properties of these peptides.

iv. Immunization protocol. Preimmune sera were obtained from mice, which were subsequently immunized intraperitoneally with 100 μg of the indicated peptide with RIBI adjuvant (MPL+TDM+CWS) (Sigma Immunochemicals). Animals were boosted twice at two week intervals using the same injection procedure. Sera were obtained following three immunizations (at 6 weeks).

V. Analysis of serum antibody responses. For radioimmunoassay (RIA), anti-peptide antibodies were determined, before and at different time points after immunization, in 96-well microtiter plates (Dynatech Laboratories, Inc.). Plates were coated with 50 μl of a 100 μg/ml appropriate peptide in phosphate-buffered saline (PBS) pH 7.4 solution overnight at 4° C. The wells were blocked by incubation with 5% dry milk in PBS pH 7.4 for at least two hours. Anti-peptide antibody titers were determined using serial dilutions of sera. The sera were diluted with PBS containing 0.05% Tween-20, pH 7.4 (washing buffer) and 50 μl of each dilution was incubated at 37° C. for 1 hour. The wells were then drained, washed 4 times with PBS-Tween and 50 μl of $^{125}$I-goat anti-mouse Ab (1–2×$10^4$ cpm/well) was added and incubated for 1 hr at 25° C. After washing, specific radioactivity was recorded in a gamma counter (1272 Clini-Gamma, LKB).

Anti-peptide antibody isotype titers were determined by enzyme-linked immunosorbent assay (ELISA) carried out in 96-well microtiter plates. The plates were coated with 100 μg/ml of appropriate peptide in PBS, pH 7.4, and incubated overnight. The wells were blocked with 5% dry milk in PBS pH 7.4 for at least two hours. Anti-peptide titers were determined using serial dilutions of sera as described above. After the plates were washed 4 times, 50 μl of a 1:100 dilution of rabbit anti-mouse IgA, IgG1, IgG2a, IgG2b, IgG3 and IgM (Zymed) was added to each well and incubated at 25° C. for 1 hour. The plates were washed 4 times with washing buffer and 50 μl of 1:500 goat anti-rabbit conjugated to peroxidase (Zymed) was incubated at 37° C. for 1 hour. Again, the plates were washed 4 times with washing buffer and bound enzyme was detected by the addition of 50 μl 1 mg/ml p-nitrophenyl phosphate (Sigma) in 10% diethanolamine (Sigma) pH 9.4. The reaction was stopped by the addition of 50 μl of 0.5 M sodium hydroxide and absorbance values ($A_{405}$) were determined on Titertek Multiskan (Flow Laboratories, Irvine, Scotland).

vi. Experimental groups. Experimental groups were as follows:

Group A. mice immunized with peptide (1)

Group B. mice immunized with peptide (2)

Group C. mice immunized with peptide (1) plus peptide (2)

Group D. mice immunized with peptide (3)

Group E. mice immunized with peptide (4).

Figure 2:
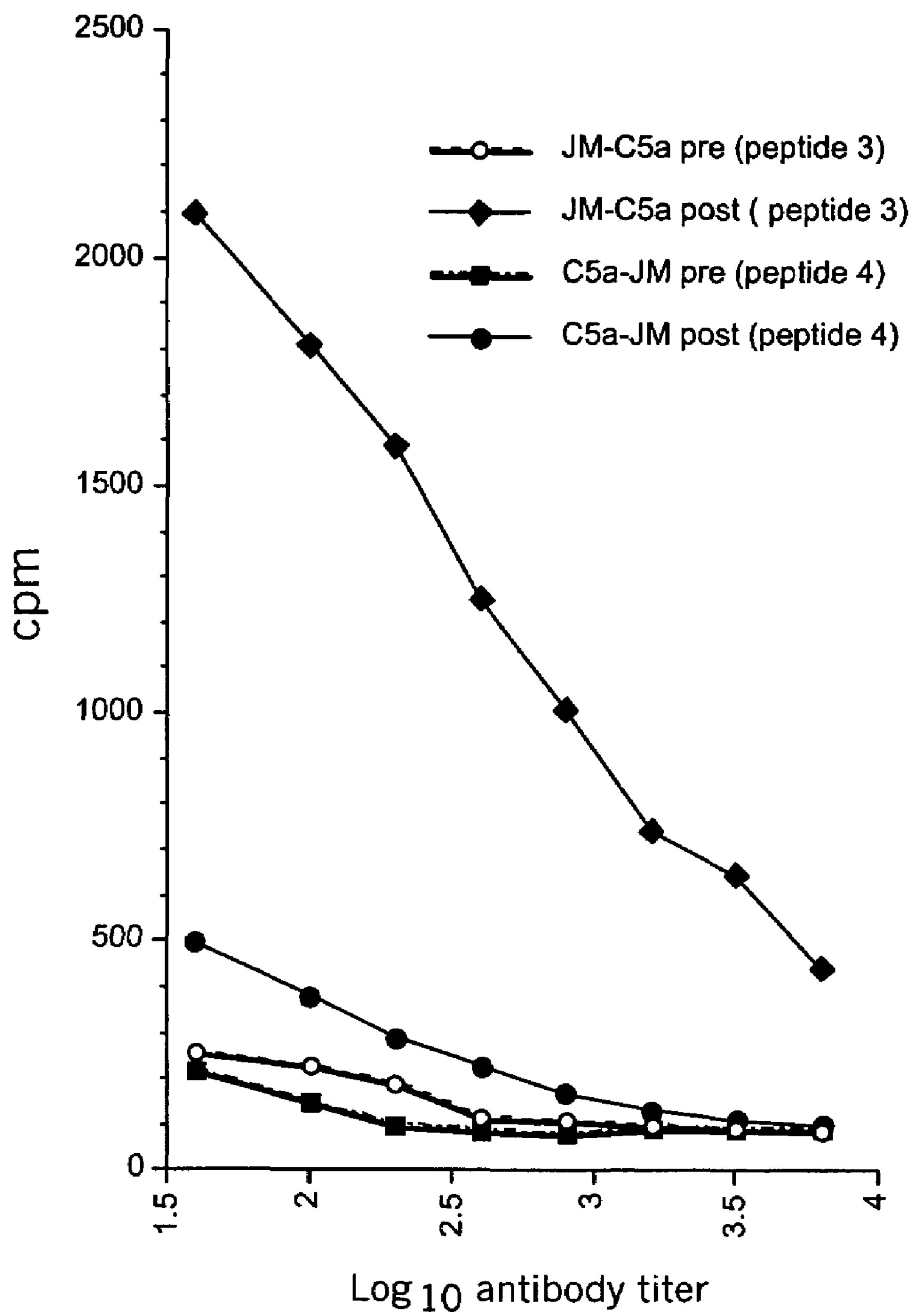
FIG. 2 is a graph illustrating the increase in antibody titer in the sera of mice collected either before (pre) or after immunization with peptides 3 (YKQGGFLGLYSFKPMPLaR; SEQ ID NO:2) and 4 (YSFKPMPLaR-KQGGFLGL; SEQ ID NO:5) as determined by radioimmunoassay and shows the relationship between the amount of $^{125}$I-goat anti-mouse antibody bound and the dilution factor of mouse sera which had been incubated in microtiter wells coated with MUC1 epitope peptide. Note that peptides 3 and 4 comprise two moieties, a targeting ligand and an antigen to which an immune response is desired.

The results of the experimental protocols are set forth in FIGS. 1 and 2. As can be seen in the Figures, the mice in Groups A, B, C and E produced no appreciable increase in antibody response to inoculation with MUC1 epitope (Group A), C5a agonist peptide (Group B), MUC1 epitope combined with, but not conjugated to, C5a agonist peptide (Group C), or MUC1 epitope conjugated to the C5a agonist peptide at its C-terminus, rather than its N-terminus (thereby blocking C5a biological activity) (Group E). Only mice inoculated with the MUC1 epitope/C5a agonist peptide conjugate of the present invention (Group D) generated an appreciable antibody response. Furthermore, this stimulation was significant. It is clear from these results that inoculation with the conjugated MUC1 epitope/C5a agonist peptide was far more efficient in stimulating a general immune response (i.e, production of antibodies) than was inoculation with either peptide alone, or both peptides together, but not conjugated, or peptides conjugated in the opposite orientation.

There are several significant conclusions that can be drawn based on these results. The fact that both Balb/c and C57B16 mice showed antibody responses to peptide 3 suggests that the antigen presenting effect is not restricted by MHC haplotype. The fact that immune responses were not produced to peptide 4, or to mixtures of peptide 1 and 2, but that substantial responses were produced to peptide 3, suggest that the effect is mediated by the C5a moiety of the peptide and that the immune response results from the simultaneous delivery of antigen peptide and C5a mediated activation signals to antigen presenting cells.

Figure 3:
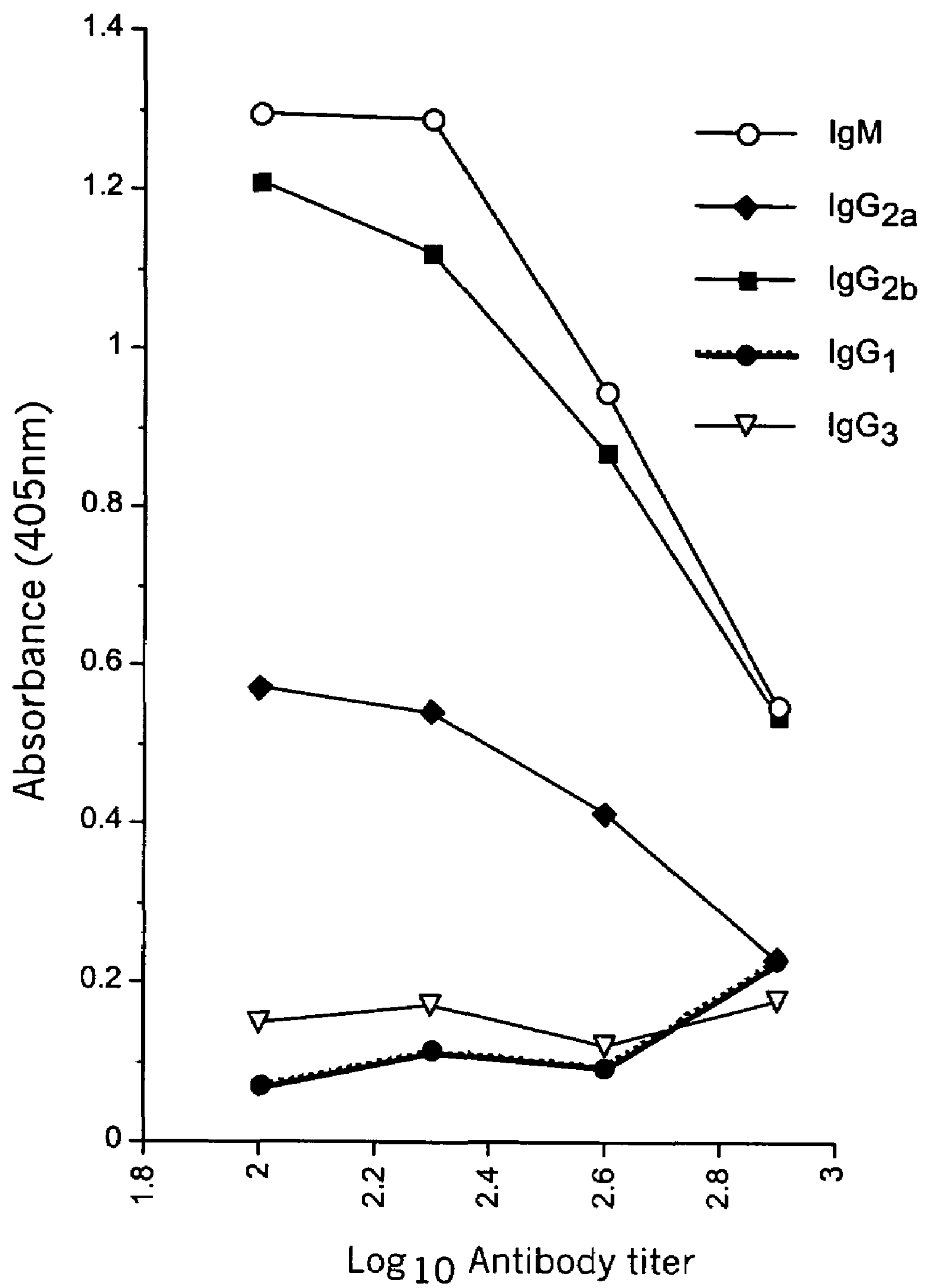
FIG. 3 is a graph illustrating the titers of antibody classes and subclasses produced in mice following immunization with peptide 3 (YKQGGFLGLYSFKPMPLaR; SEQ ID NO:2) as determined by ELISA using rabbit anti-mouse IgA, IgG1, IgG2a, IgG2b, IgG3, and IgM, followed by goat anti-rabbit conjugated to peroxidase and detected using p-nitrophenyl phosphate cleavage monitored at 405 nm.
Figure 4:
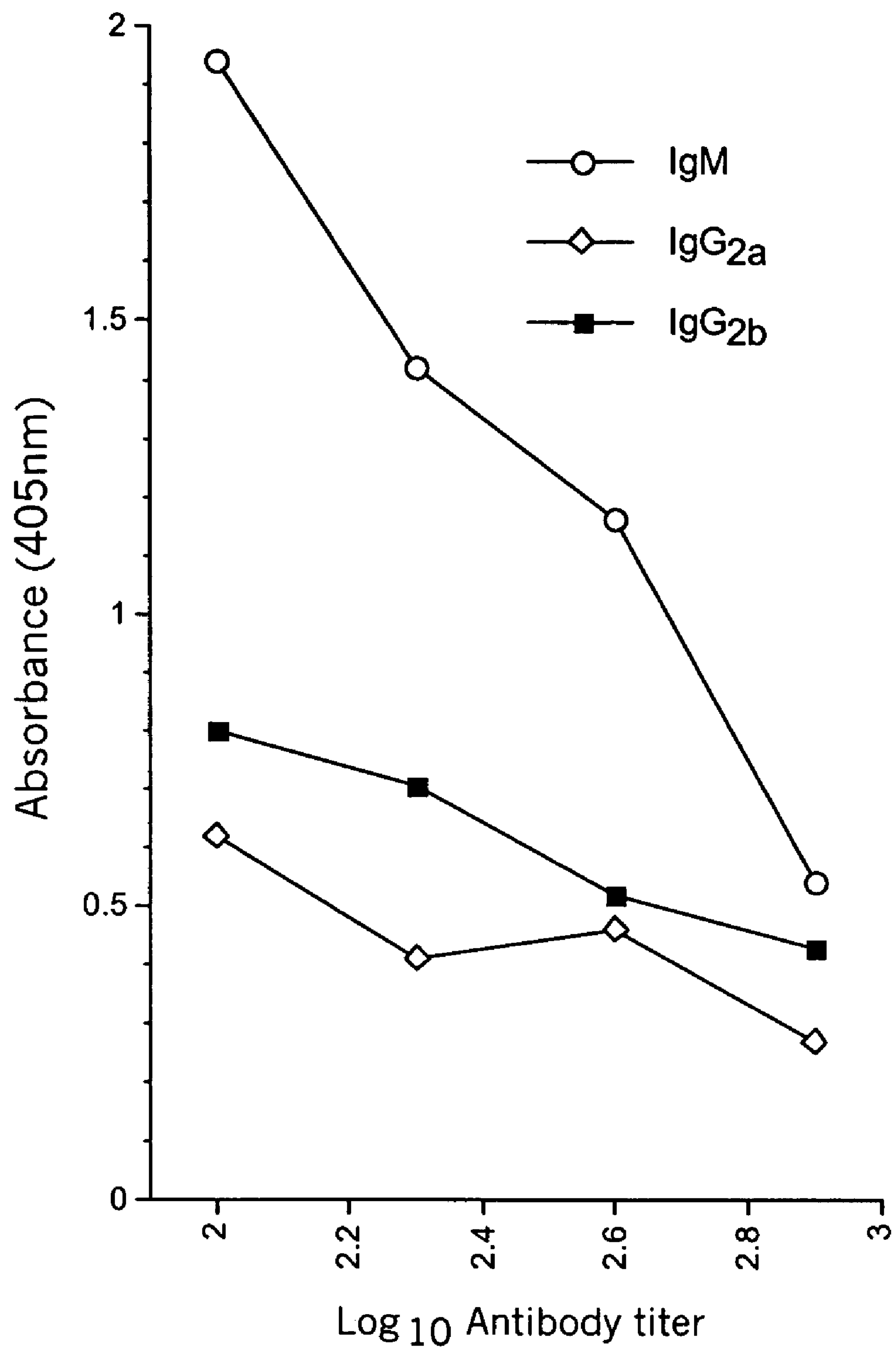
FIG. 4 is a graph illustrating the specificity of binding of the antibody subclasses in sera from mice immunized with peptide 3 (YKQGGFLGLYSFKPMPLaR; SEQ ID NO:2) as determined by ELISA using binding to microtiter wells coated with MUC1 epitope peptide and detection with rabbit anti-mouse IgG2a, IgG2b, or IgM followed by incubation with goat anti-rabbit conjugated to peroxidase and detected using p-nitrophenyl phosphate cleavage monitored at 405 nm.
Figure 5:
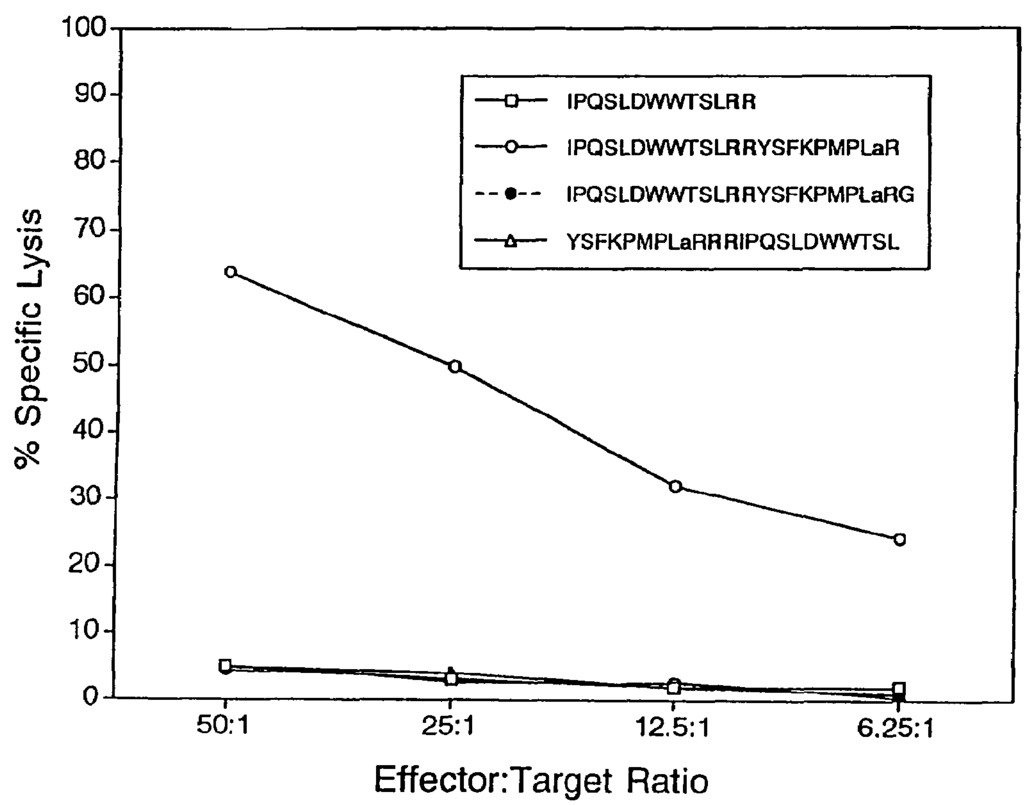
FIG. 5 is a graph showing that HBsAg-specific CTL response is induced only by C5a-active constructs. BALB/c mice received three s.c. injections at 21 day intervals using 50 μg doses of the HBsAg-$L^d$ MHC class I restricted peptide ($S_{28-39}$) synthesized with two Arg residues appended to the C-terminal end (IPQSLDSWWTSLRR; SEQ ID NO:18), the double-Arg-linked C5a-active construct (IPQSLDSWWTSLRRYSFKPMPLaR; SEQ ID NO:14) and the double-Arg-linked C5a-inactive constructs (IPQSLDSWWTSLRRYSFKPMPLaRG; SEQ ID NO:17 and YSFKPMPLARRRIPQSLDSWWTSL; SEQ ID NO:16). Pooled spleen cell suspensions were prepared from two mice in each group 14 days following the third injection. The cell suspensions were cultured in the presence of the $S_{28-39}$ peptide (75 nM) for four days and used as effector cells against $^{51}$Cr-labeled P815S (HBsAg transfectant) or P815 targets. Percent specific lysis of $^{51}$Cr labeled P815S cells at various effector to target ratios is shown and represent the means of triplicate determinations. Lysis of $^{51}$Cr labeled P815 cells at an effector-to-target ratio of 50:1 was less than 5% (not shown). The data are representative of three separate experiments.

The isotypes of the anti-peptide antibodies produced in the immunized mice were determined (FIG. 3) and were found to consist of IgM, IgG2a, and IgG2b. This suggests that the immunogenic peptide is producing T cell-dependent responses, which generally require antigen processing and presentation. Data presented in FIG. 4 show that the antibody response to peptide 3 includes a high percentage of antibodies that are specific for the MUC1 epitope that was the antigen moiety of these studies.

EXAMPLE 2

Evaluation of Serum Amyloid A/C5a Peptide Conjugates for Recruitment and Activation of APCs and Stimulation of Immune Response in Rats Serum amyloid A is an acute-phase stress response protein generated by the liver. Along with other acute phase proteins, SAA is secreted in response to systemic inflammatory stress as a protective measure. SAA is of interest because it appears to be an excellent indicator of general, systemic inflammation, which is a phenomenon that is very difficult to quantitate. Because serum levels of SAA have been observed to parallel the rise and fall of the systemic inflammatory response, quantitation of serum levels of this peptide would provide an effective means of assessing inflammation. One way to accomplish this is to develop antibodies against SAA that could be used for quantitation such as in an ELISA assay. However, SAA has been particularly recalcitrant to the generation of antibodies against it. In this example, an evaluation was made of the ability of SAA conjugated to a C5a C-terminal analog (as described in Example 1) to activate antigen producing cells and produce an antibody response in rats.

i. Production and preparation of proteins and peptides. The C-terminal C5a analog K-Ahx-YSFKPMPLaR (SEQ ID NO:8) (AhX is aminohexanoic acid, which is a linear aliphatic spacer moiety) was produced as described in Example 1. The aliphatic spacer moiety was included to separate the critical receptor-binding C5a analog from the bulky protein to be attached to the amino terminus.

Serum amyloid A was conjugated to the C5a peptide analogs according to the following method. SAA (100 μg) was reacted with a 50-fold molar excess of a water soluble carbodiimide, 1-(3-dimethylaminopropyl)-3-ethylcarbodiimide methiodiide (EDC), in 200 μl of phosphate buffered saline, pH 7.5, at room temperature for 30 minutes. A 50-fold molar excess of the peptide (K-Ahx-YSFKPMPLaR; SEQ ID NO:8) and a 100-fold molar excess of a base diisopropylethyl amine (DIEA) were added to this solution. Water was added to the solution to bring the reaction mixture to a volume of 400 μl. This solution was stirred overnight at room temperature and then lyophilized to a dry powder. The powder was diluted to the appropriate volume with water to generate the stock mixture used for inoculating the animals.

ii. Experimental protocols. Rats were injected intraperitoneally with an inoculant comprising the SAA/C5a peptide conjugates in phosphate-buffered saline with or without RIBI adjuvant. Booster injections were given two and five weeks after the initial injections. The rats were sacrificed seven weeks after the initial injection and anti-mucin antibody production was assessed from the serum titers, as described in Example 1.

Significant anti-SAA antibody was produced from both groups of rats, whether or not RIBI adjuvant was included in the inoculation. As visualized by gel electrophoresis and autoradiography of anti-SAA antibody eluted from the plate assays, it appeared that anti-SAA antibody titers were essentially equivalent, or slightly higher, in rats inoculated with SAA/C5a peptide conjugate in the absence of RIBI adjuvant as compared to the same inoculation without the adjuvant. Thus, antigenic conjugates comprising the C5a peptide analog are useful for generating antibodies against large proteins, as well as against smaller peptide fragments, such as those described in Example 1. Moreover, the successful generation of anti-SAA antibodies utilizing this method is particularly promising for purposes of producing antibodies against weakly- or non-antigenic peptides or proteins.

EXAMPLE 3

Production and Characterization of Site-Directed Neutralizing Antibodies Specific for a Peptide κR(33-52) from the Predicted Amino-Terminal Region of the Human Kappa Receptor Receptors for human opioid peptide hormones have been described on numerous cell types. The receptors for μ, κ, and δ ligands have recently been cloned from genomic and cDNA libraries derived from normal tissue and cell lines. Considerable homology exists among the μ, κ, and δ receptors, except for the N-terminal regions of the receptors. The N terminal region of the human kappa receptor (amino acid residues 1–100) is relatively hydrophilic and would be predicted to be exposed on the surface of the cell membrane. A 20 residue peptide [κR(33-52)], was chosen and used to raise a site directed peptide specific polyclonal antibody (5).

The method of production of a polyclonal antiserum in rabbits using the molecular adjuvant, C5a-agonist peptide conjugated to the κR epitope is set forth below. The binding specificity and biological activities of the resulting polyclonal antiserum raised to the predicted extracellular region of the human kappa receptor (κR) are also described below.

i. Construction of Targeted-Immunogen. A peptide construct consisting of the κR(33-52) (FPGWAEPDSNGSAGSEDAQL; SEQ ID NO:9) covalently attached to the N-terminal end of a conformationally biased, C5a complement fragment agonist analogue peptide (YSFKPMPLaR; SEQ ID NO:1) was synthesized according to the methods in Example 1 and as previously reported (7).

ii. Preparation of anti-κR(33-52) Antiserum and Peptide-Specific ELISA. Rabbits were immunized s.c. with 500 μg of FPGWAEPDSNGSAGSEDAQLYSFKPMLaR (SEQ ID NO:10) construct in complete Freund's adjuvant (GIBCO, Grand Island, N.Y.) on day O followed by booster injections on days 30 and 60 in incomplete Freund's adjuvant. Serum was collected starting 75 days after the initial immunization.

The presence of anti-peptide antibody was determined by using a peptide specific ELISA utilizing the free κR(33-52) peptide as previously described (8). Anti-κR(33-52) and normal rabbit γ-globulin (RGG) were purified by protein A Sepharose chromatography (Sigma) (8) prior to use.

iii. Cells and culture conditions. The neuroblastoma cell SK-N-SH (HTB 11), ductal breast cell carcinoma T47D (HTB 133), Jurkat T cell leukemia, (TIB 152), U937 histolytic lymphoma (CRL1593), THP 1 human monocyte (TIB 202), EBV-transformed B cells SKW 6.4 (TIB 215) and CESS (TIB 190) (American Type Culture Collection, Rockville, Md.) were cultured in DMEM or RPMI 1640 supplemented with 10% fetal calf serum, 25 mM HEPES, 1 mM L-glutamine, 2 mM Na pyruvate, 50 U penicillin and 50 μg/ml streptomycin. The human neuronal precursor cells NT2 (Stratagene, La Jolla, Calif.) were cultured in Opti-MEM (Gibco) supplemented as above. All cultures were incubated at 37° C. in a humidified chamber with 7.5% $CO_2$.

Peripheral blood derived mononuclear cells were obtained from healthy male and female volunteers, isolated by Ficoll-Hypaque(™) density gradient centrifugation and enriched for macrophage by adherence to plastic.

iv. Flow Cytometry. Single-color flow cytometry analysis of cells ($1\times10^6$) in PBS containing 1% bovine calf serum and 0.1% sodium azide (staining buffer) were preincubted 30 minutes at 4° C. in the presence of 20% normal human serum. The cells were washed and then incubated with anti-κR(33-52) or RGG for 30 minutes at 4° C., washed and labeled with PI-conjugated donkey (Fab')2 fragments of antirabbit IgG (Zymed, S. San Francisco, Calif.) for 30 minutes at 4° C. (8). For dual color analysis FITC-conjugatd anti-CD3 or anti-CD14 (Pharmingen, San Diego, Calif.) were also included in the second step. Cells ($1\times10^4$) were analyzed on a FACScan (Becton Dickinson, Mountain View, Calif.) and data were analyzed with the Cell Quest software as previously described (8).

V. Measurement of cell proliferation. Peripheral blood mononuclear cell (PBMC) were pulsed on day 2 of culture with $^3$H-thymidine and 18 hours later the cells harvested on glass fiber filters and processed for scintillation counting. Experiments were performed three times and each sample done in triplicate.

vi. Measurement of IgG Secretion. Relative levels of IgG in culture supernatants were determined by an indirect ELISA as previously described (9). Supernatant derived from PBMC cultures were collected after 10 days and assayed for the presence of IgG. Numbers represent the mean CPM+/−SD from triplicate samples. Experiments were performed at least three times.

vii. Characterization of Anti-κR Peptide Antisenum. Serum from rabbits immunized with the κR(33-52)YSFPMPLaR (SEQ ID NO:10) construct and normal rabbit serum were assayed for the ability to recognize plate bound κR(33-52) (SEQ ID NO:9) in ELISA. The results show that serum from rabbits immunized with the κR(33-52)YSFPMPLaR (SEQ ID NO:10) construct bound free κR(33-52) SEQ ID NO:9) peptide in a dose dependent fashion. The titer was approximately $10^5$. In contrast, serum from unimmunized rabbits failed to bind this peptide. Serum samples from immunized and unimmunized rabbits were subjected to protein A-Sepharose chromatography and the column eluates were assessed for κR(33-52) (SEQ ID NO:9) specific antibody. The results indicate that protein A-purified antibody derived from rabbits immunized with the κR(33-52) YSFPMPLaR (SEQ ID NO:10) construct binding to free κR(33-52) (SEQ ID NO:9) was detectable at antibody concentrations less than 0.1 ng/ml. In contrast, RGG failed to bind the free peptide. The results from multiple bleedings indicated that the $ED_{50}$ titer ranged between 1–10 ng/ml. These results indicate that rabbits immunized with KR(33-52)YSFPMPLaR (SEQ ID NO:10) contained high titer, κR(33-52) peptide specific antibody.

viii. Binding of anti-R (33-52) antibody to cells expressing human κR. To determine whether the polyclonal anti-κR(33-52) antibodies bound to cells expressing the κR, a variety of mononuclear cell lines and normal human mononuclear cells were first assayed for the presence of the κ receptor specific mRNA by RT-PCR. RNA samples isolated from neuronal cell lines NT2, U937, Jurkat, T47D, normal human PBMC, and enriched human macrophage were subjected to RT-PCR analysis with 5' sense and 3' antisense primers specific for the 3' region of the cloned κR and B-actin. All of the cell lines or cell fractions, except for the T47D cell line, were positive for the κ-receptor specific PCR product, as expected based on the primer sequences used (5).

Experiments were performed to determine whether anti-κR(33-52) bound to cells expressing κR specific mRNA. The results of single color flow cytometric analysis for several cell lines are shown in Table 2. Flow cytometric measurements were conducted with human cell lines representative of macrophage (U937), T lymphocytes (Jurkat), and B lymphocytes (SKW 6.4 and CESS). The results indicate that anti-κR(33-52) bound all three cell types. Anti-κR(33-52) bound to U937 cells to the greatest extent (MFI=231) compared to normal RGG (MFI=38). As used herein MFI refers to mean fluorescence intensity. Comparison of anti-κR(33-52) and RGG binding to the Jurkat line indicated approximately a 3-fold shift in MFI (MFI=18 vs. MFI=6). Similar results were obtained with the two B lymphocyte-like cell lines (SKW 6.4 and CESS). Comparison of anti-κR(33-52) and RGG binding to the SKW 6.4 line indicated approximately a 3-fold shift in MFI (MFI=19 vs. MFI=6). The neuronal cell line was also specifically bound by the anti-κR(33-52) as indicated by a 3-fold shift in the MFI over the RGG. Finally, based on the lack of expression of κR-specific mRNA from the human breast carcinoma cell line (T47D), this cell line was assessed for its ability to bind to anti-κR(33-52) by flow cytometric analysis. The lack of a κR expression on T47D cells was confirmed by the fact that anti-κR(33-52) and RGG bound to these cells in an almost identical fashion. As a positive control, anti-κR(33-52) and RGG were assessed for their ability to bind to an additional human macrophage-like cell line (THP 1). Comparison of anti-κR(33-52) and RGG binding to this cell line resulted in a significant shift in MFI (MFI=190 vs. MFI=8). These results confirm the specificity of anti-κR(33-52) for the human κR.

TABLE 1

Selected cell type binding of anti-κR(33-52) antibodies produced in rabbits immunized with C5a-agonist peptide conjugated to the κR(33-52) sequence as assessed by single channel color flow cytometric analysis.

| | Mean Channel Intensity | | |
|---|---|---|---|
| Cell Line | Cell Type | RGG | anti-κR Ab |
| NT2 | Neuronal | 9 | 19 |
| U937 | Macrophage | 38 | 231 |
| Jurkat | T-lymphocyte | 6 | 18 |
| SKW 6.4 | B-lymphocyte | 6 | 19 |
| CESS | " | <10 | >10 |
| Controls T47D (negative) | Human Breast Carcinoma | ~3 | ~3 |
| THP1 (positive) | Macrophage | 8 | 190 |

Analysis of intact human PBMC indicated that these cells express mRNA for a "κ-like" R (5). Dual color flow cytometric analysis was utilized to assay for the binding of anti-KR(33-52) to normal human macrophage (CD14+) and T lymphocytes (CD3+). It was observed that both macrphage and T lymphocytes bound anti-κR(33-52) antibody. Anti-κR(33-52) and RGG were assessed for binding to CD14+ PBMC. The results indicate that anti-κR(33-52) bound CD14+ cells with a 15-fold increase compared to normal RGG (MFI=320 vs. MFI=21). Anti-κR(33-52) was also found to bind CD3+ cells (MFI=19 vs. RGG MFI=3) albeit less than CD14+ cells. These results indicate that anti-κR(33-52) binds normal PBMC-derived mononuclear cells as well as mononuclear cell lines, which express κR-specific mRNA.

ix. Neutralization of U50,488H-mediated suppression of lymphocyte proliferation by anti-κR(32-52) antibody in vitro. The results of published studies have shown that opioid peptide-induced regulation of in vitro immune responses can occur via specific receptor-ligand interactions. More specifically, it has been shown that the κR-selective agonist U50,488H is capable of suppressing SAC-induced lymphocyte proliferation by human PBMC cultures (6). The inhibition of lymphocyte activation by U50,488H has also been shown to be reversed by the κR-selective antagonist nor-BNI. To determine whether anti-κR(33-52) was capable of acting as an κR selective antagonist and neutralizing U50,488H-mediated suppression, PBMC cultures were preincubated with various concentrations of protein A purified anti-κR(32-52) prior the addition of SAC and U50,488H. U50,488H suppresses SAC-induced lymphocyte proliferation in a dose dependent fashion (5). Maximal suppression was obtained when U50,488H was used at a concentration of $10^{-6}$ M. PBMC cultures were preincubated with various concentrations of anti-κR(33-52) (1–50 μg/ml), followed by the addition of U50,488H plus SAC, and proliferation measured on day 3 of culture. Anti-κR(33-55) was found to neutralize U50,488H-mediated suppression of SAC-induced lymphocyte proliferation in a dose dependent fashion. In contrast, identical concentrations of normal RGG failed to inhibit κR selective agonist mediated immunosuppression.

Since SAC has been shown to induce both T and B lymphocyte proliferation, similar experiments were conducted with the T cell mitogen PHA. Anti-KR(33-52) was also able to neutralize the ability of U50,488H to suppress mitogen-induced T cell proliferation. U50,488H ($10^{-6}$ M) suppressed PHA-induced T cell proliferation by 85%. This suppression was reversed by preincubating the cells with anti-κR(33-52). Preincubation of PBMC with normal RGG failed to block U50,488H-mediated suppression of T cell proliferation.

Anti-κR(33-52) does not appear to directly modulate lymphocyte proliferation. The co-culture of PBMC with anti-κR(33-52), in the absence of mitogen, failed to stimulate the cells above the media control. Moreover, the combination of antiκR(33-52) and PHA or SAC did not result in increased cell proliferation compared to PBMC cultures receiving mitogen only.

x. Neutralization of U50,488N-mediated suppression of IgG synthesis by anti-κR(32-52) antibody in vitro. In addition to lymphocyte proliferation, U50,488H is a potent inhibitor of SAC-induced IgG synthesis in human PBMC cultures (6). To determine whether anti-KR(32-52) was capable of neutralizing the suppression of IgG synthesis, PBMC were preincubated with anti-κR(32-52) followed by the addition of U50,488H and SAC, and IgG levels measured on day 10. Results indicate that U50,488H at $10^{-8}$ M and $10^{-7}$ M inhibited IgG synthesis by 67% and 85% respectively (5). The inclusion of anti-κR(32-52) in culture was found to neutralize suppression of SAC induced IgG synthesis in a dose dependent manner. In contrast, similar concentrations of normal RGG failed to neutralize the observed suppression.

To assess the specificity of anti-κR(32-52) antibody, PBMC were incubated with specific antibody or RGG followed by co-culture with U50,488H or the μ receptor selective agonist (DAGO) and IgG production measured by ELISA. The results indicate that, whereas, anti-κR(32-52) neutralized U50,488H-mediated inhibition of SAC-induced IgG synthesis, anti-κR(32-52) was unable to neutralize DAGO-mediated suppression of IgG synthesis.

These results indicate that in addition to binding lymphocytes and macrophage, anti-κR(32-52) is capable of neutralizing the ability of a κR selective agonist (U50,488H), but not a μR selective agonist (DAGO). Additionally the antibody demonstrated significant inhibition of both lymphocyte proliferation and differentiation to antibody synthesis. These results further demonstrate the specificity of anti-κR(33-52) for the human kappa receptor.

As can be seen from the antibody binding data presented above, the site directed polycolonal antibodies raised in rabbits using the C5a-agonist form of the molecular adjuvant conjugated to the κ receptor sequence were capable of binding to normal human cells and cell lines expressing mRNA specific for the human κ receptor. Flow cytometric analysis of a neuronal cell line (NT2), normal blood-derived CD14+ monocytes, monocyte-like cell ines (U937 and THP1), normal blood derived CD3+ T cells and a T cell line (Jurkat), and human B cell lines (SKW6.4 and CESS) revealed that the cells were all bound by anti-κR(33-52) in a specific manner. The anti-κR(33-52) did not bind to a cell line determined not to express mRNA for the human κ receptor.

Anti-κR(32-52) was found to specifically neutralize κR-selective agonist (U50,488H)-mediated inhibition of lymphocyte activation. The antiserum was found to neutralize, in a dose dependent manner, U50,488H-mediated inhibition of: 1) SAC-induced lymphocyte proliferation; 2) PHA-induced lymphocyte proliferation and; 3) SAC-induced IgG synthesis. In contrast, DAGO-mediated suppression of SAC-induced IgG production was not affected by anti-κR(32-52). These results suggest that this site directed polyclonal antiserum specifically interacts with the human KR on PBMC. The results presented indicate that polyclonal anti-κR(32-52) antibodies interact with the exposed N-terminal region of the κR. While this antiserum effectively blocked U50,488H-mediated lymphocyte activation, it did not activate macrophage or lymphocytes.

While anti-K opioid receceptor antibodies are exemplified above, conjugation of C5a agonist peptide to peptides corresponding to μ and Δ specific peptides has resulted in the successful generation of specific antibodies to the μ and Δ epitopes.

EXAMPLE 4

Comparison of Immunogenicity of Epitope-C5a Agonist Constructs with Epitope-KLH Conjugates The following experiment was performed in order to compare the potency of the molecular adjuvant of the present invention with a widely used method for enhancing the immune response to peptide epitopes. The objective was a direct comparison of the response to a construct of MUC1 epitope-C5a agonist and the same epitope conjugated to keyhole limpet hemocyanine (KLH) in mice. The results are summarized in Table 2.

TABLE 2

MUC1 Specific Ab Isotype Titers Produced with Different Immunogens.

| | Ab Isotypes and Titers[a] | | | | | |
|---|---|---|---|---|---|---|
| | IgA | IgG1 | IgG2a | IgG-2b | IgG3 | IgM |
| YKQGGFLGLYSFKPMP LaR[b] (SEQ ID NO: 2) | 0 | 0 | 1260 (5/5) | 1780 (5/5) | 0 | 6310 (5/5) |
| YKQGGFLGL-KLH[c] (SEQ ID NO: 6-KLH) | 0 | 100 (2/5) | 0 | 0 | 0 | 5010 (4/5) |

[a]Sera were screened against MUC1 peptide and mean titer values of responders are shown. Parentheses indicate the number of responders. Ab titer is defined as the sera dilution within the linear range at which specific reactivity is lost.

TABLE 2-continued

| MUC1 Specific Ab Isotype Titers Produced with Different Immunogens. | | | | | | |
|---|---|---|---|---|---|---|
| | Ab Isotypes and Titers[a] | | | | | |
| | IgA | IgG1 | IgG2a | IgG-2b | IgG3 | IgM |

[b]Five C57BL6 mice were immunized and boosted with YKQGGFLGLYS-FKPMPLaR (SEQ ID NO: 2) and sera were obtained as indicated in the Material and Methods section. Standard error of responder titer values was less than 32% for all isotypes.
[c]Five C57BL6 mice were immunized and boosted with YKQGGFLGL-KLH (SEQ ID NO: 6-KLH) and sera were obtained as indicated in the Materials and Methods section. Standard error of responder titer values was less then 25% for IgM and less than 40% for IgG1.

A similar experiment was performed in rabits. The immunogens used in rabbits were the κ- and μ-opioid receptor epitopes, FPGWAEPDSNGSEDAQL (SEQ ID NO:9) and GDLSDPCGNRTNLGGRDSL (SEQ ID NO:11), respectively. The serum antibody titer and antibody subtypes produced in rabbits injected with the two compositions containing the different immunogens were compared.

i. Peptide conjugates. In one instance the epitopes were conjugated to KLH via a lysine residue added synthetically to the N-terminus of the epitope along with an alanine residue which acted as a spacer. In this experiment, glutaldehyde was used to effect conjugation. In the another case, the epitopes were linked to the N-terminal end of the C5a agonist YSFKPMPLaR (SEQ ID NO:1) using the solid phase peptide synthetic methodologies described above in example 1.

ii. Immunization protocol for rabbits. Rabbits were immunized s.c. with 500 μg of either the epitope-KLH or the epitope-YSFKPMPLaR (epitope-SEQ ID NO:1) constructs in compete Freund's adjuvant (GIBCO, Grand Island, N.Y.). Booster injections were administered on days 30 and 60 in incomplete Freund's adjuvant. Serum was collected starting at day 60 post-immunization.

iii. Antibody determination. The presence of rabbit IgG specific for the peptide epitopes was determined by ELISA as previously described (8). Rabbits immunized with the epitope-C5a agonist generated high titer IgG Abs specific for the opioid receptor peptide epitopes. The rabbits immunized with the opioid receptor epitopes conjugated to the carrier protein KLH also produced high titer antibodies specific epitopes to which they were injected. These results demonstrate that the decapeptide C5a-agonist was as effective as the large molecular weight protein, KLH, conjugated to the epitope at inducing specific anti-peptide antibodies in non-rodent species.

EXAMPLE 5

Evaluation of C5a Peptide to Function as a Molecular Adjuvant and Epitope Delivery System for a Defined CTL Epitope of Hepatitis B Virus Surface Antigen Experiments were performed in which YSFKPMPLaR (SEQ ID NO:1) was used as a molecular adjuvant for inducing Ag-specific CTL responses against a defined CTL peptide epitope from the hepatitis B surface antigen (HBsAg). The HBsAg CTL epitope was covalently attached to either the N-terminus of YSFKPMPLaR (SEQ ID NO:1) (C5a-active constructs) or to its C-terminus (C5a-inactive constructs). Mice were immunized with these C5a-active and C5a-inactive constructs in the absence of any added adjuvant in order to evaluate the ability of YSFKPMPLaR (SEQ ID NO:1) to provide the necessary signals and/or targeting required for the induction of an Ag-specific CTL response. Immunizations were also performed with C5a-active constructs containing protease-sensitive linker sequences between the HBsAg CTL epitope and the C5a agonist. The results of these experiments were analyzed in terms of a possible mechanism by which YSFKPMPLaR (SEQ ID NO:1) induces Ag-specific CTL responses and the importance of a protease-sensitive sequence between the epitope and the C5a agonist.

Materials and Methods:

Peptide synthesis. Peptides were synthesized by standard solid phase methodologies on an Applied Biosystems (Foster City, Calif.) model 430A synthesizer. Syntheses were performed on a 0.25-mmol scale and employed the Fmoc (9-fluorenylmethyloxycarbonyl) method of repetitive residue linkages. Peptide purification was accomplished with analytical and preparative HPLC on columns packed with $C_{18}$-bonded silica. All peptides were characterized by amino acid compositional analysis and mass spectrometry. The details of these methods of synthesis, purification, and characterization have been described previously (Sanderson et al., J. Med. Chem. 37, 3171, 1994).

Pharmacologic assays. C5a-like agonistic activity was assessed by the ability of the peptides to induce smooth muscle contraction of human umbilical artery and MPO release from human PMNs according to previously published methods (Sanderson et al., 1994, supra; Sanderson et al., J. Med. Chem. 38, 3669, 1995; Finch et al., J. Med. Chem. 40, 877, 1997). Full concentration-response curves were generated for individual peptides and natural C5a in each assay and the $EC_{50}$ values (the concentration of peptide producing 50% of the maximal response to each peptide) were calculated. $pD_2$ transforms [$-\log EC_{50}$ (M)] were calculated for each concentration-response curve and reported as the mean ±SE. Peptide binding affinity to the C5aR was evaluated on intact human PMNs by a competition assay using $^{125}$I-C5a according to previously described methods (Sanderson et al., 1995, supra; Finch et al., 1997, supra). Statistical analysis of the values obtained from pharmacologic assays was performed using one-way analysis of variance (ANOVA).

Animals. Female BALB/c (H-$2^d$) mice 10 to 12 weeks old were purchased from the Jackson Laboratory (Bar Harbor, Me.). On arrival, mice were housed in isolator cages, provided autoclaved food and water ad libitum, and quarantined for seven days. On release from quarantine, the mice were entered into the study following written protocols on file with the Animal Care and Use Committee and in compliance with the Animal Welfare Regulations (9CFR).

Immunization protocols. Groups of six to eight BALB/c mice were given bilateral s.c. injections in the inguinal area with (100 μl each side) of a PBS solution containing 50–100 μg of the peptides. Booster injections were given s.c. in the inguinal region at 21-day intervals. Sera for Ab analysis were obtained by retro-orbital bleeds of mice under $CO_2$ narcosis.

Spleen cell cultures and in vitro stimulation. Three weeks after secondary (2°) immunization and two weeks after tertiary (3°) immunization, two to three mice from each experimental group were sacrificed by cervical dislocation and their spleens removed aseptically. Pooled splenic single-cell suspensions were prepared in RPMI-1640 medium (Sigma, St. Louis, Mo.) containing 10% FBS (Hyclone, Salt Lake City, Utah) and the following supplements: 10 mM HEPES buffer, 50 μM 2-ME, 2 mM L-glutamine, 50 μg/ml gentamicin sulfate, 100 U/ml penicillin, and 50 μg/ml streptomycin (all supplements from Sigma). This supplemented complete medium is designated RP10-SC. For culture, $75\times10^6$ pooled spleen cells in 5 ml of RP10-SC were pipetted into a 25 $cm^2$ T-flask (Corning). Next, 5 ml of RP10-SC containing 150 nM of synthetic, $L^d$ MHC class I-restricted peptide, IPQSLDSWWTSL (SEQ ID NO:12) were added to the flask. The flasks were incubated undisturbed in an upright position at 37° C. in 5% $CO_2$. After 4 days of incubation, the cells were recovered from the T-flasks, washed once by centrifugation in fresh RP10-SC, resuspended in 5 ml RP10-SC, counted, and adjusted to $5\times10^6$ viable cells/ml.

Target cell lines. The specific cell target used for measuring CTL activity was P815S, a transfectant cell line of P815 (H-$2^d$) expressing the HBsAg (14). P815S was grown in RP10-SC medium containing 400 μg/ml geneticin disulfate (G418, Sigma). The parental H-$2^d$ mastocytoma cell line, P815 (ATTC #TIB64) grown in RP10-SC medium, was used as a non-specific target for CTL assays to measure % non-specific lysis. In all the experiments shown, this value was less than 5% at effector-to-target ratios of 50:1.

Target cell labeling. The target cells, either P815S or P815, were washed 2 times in RP10-SC. For labeling, $5\times10^6$ target cells were mixed with 250 μCi $^{51}$Cr-sodium chromate [400–1200 Ci (14.8–44.4 TBq)]/g; NEN Dupont, Boston, Mass.) in a 1.0 ml volume in a 50 ml conical tube and incubated in a 37° C. water bath for 90 mins. After incubation, the labeled cells were washed 3 times by centrifugation using 15 ml volumes of fresh RP10-SC and allowed to stand at room temperature for 30 mins. The pelleted cells were resuspended in RP10-SC at $1\times10^6$ cells/ml.

Cytotoxicity assay. The recovered splenic effector cells at $5\times10^6$ cells/ml were serially diluted in triplicate in wells of round-bottom 96 well plates (Corning, 25850) in a total volume of 100 μl/well and using RP10-SC as the diluent. Next, 100 μl volumes of $^{51}$Cr-labeled targets, P815S or P815, at $1\times10^6$ cells/ml were added to the wells. Maximum release (MR) wells contained 100 μl of target cells and 100 μl of 2% (v/v) Tween 20 while spontaneous release (SR) wells contained labeled cells in medium alone. Effector-to-target ratios of 50:1, 25:1, 12.5:1, and 6.25:1 were routinely employed. The plates were centrifuged at 400× g and incubated at 37° C. in 5% $CO_2$ for 4 hrs. After incubation, the supernatant fractions in the wells were collected using a Skatron Supernatant Collection System (Skatron Instruments, Sterlin, Va.). The amount of $^{51}$Cr radioactivity in the supernatant fractions was measured using a Wallac 1470 Wizard gamma counter (Turku, Finland). Percent specific lysis was calculated as [(experimental release−SR/(MR−SR)]×100. The SR was always less than 10% of the MR. All assays were performed in triplicate.

Results:

Peptide design. Peptide immunogens were designed to evaluate the requirement for C5a agonist activity in the induction of Ag-specific CTL responses. C5a-active constructs were generated by the covalent attachment of the HBsAg CTL epitope to the N-terminus of the C5a agonist: IPQSLDSWWTSLYSFKPMPLaR (SEQ ID NO:13) IPQSLDSWTSLRRYSFKPMPLaR (SEQ ID NO:14); and IPQSLDSWWTSLRVRRYSFKPMPLaR (SEQ ID NO:15). This positioning of the CTL epitope relative to the C5a agonist leaves the biologically important conformational features expressed in the C-terminal region of YSFKPMPLaR (SEQ ID NO:1) free to interact with C5aRs expressed on the cells involved in Ag uptake and processing. The latter two peptides were designed to evaluate if predicted protease-sensitive linker sequences placed between the HBsAg CTL epitope and the C5a agonist might facilitate intracellular release of the epitope into Ag presenting pathways and thereby enhance the response. The linkers consisted of a dibasic double-Arg (RR) sequence, which is susceptible to cleavage by proteases of the subtilisin family and trypsin-like proteases. The other was a sequence sensitive to the ubiquitous intracellular subtilisin-like protease furin, RVRR (SEQ ID NO:19). This latter sequence is found at the junction of the A and B fragments of diphtheria toxin (DT) and it is believed that furin plays a prominent role in the intracellular proteolytic activation of DT and several other bacterial toxins as well as in the processing of proproteins and prohormones that contain the consensus sequence RX(K/R)R (SEQ ID NO:20). C5a-inactive constructs were generated by blocking the functionally important carboxyl group on the C-terminal Arg of YSFKPMPLaR (SEQ ID NO:1) with either the HBsAg CTL epitope, YSFKPMPLaR-RRIPQSLDSWWTSL (SEQ ID NO:16) or with a Gly residue, IPQSLDSWWTSLRRYSFKPMPLaRG (SEQ ID NO:17).

Pharmacologic activities. All peptides were evaluated for C5a agonist activities in assays that measured peptide-mediated contraction of smooth muscle in human umbilical artery (Table 3), the release of MPO from human PMNs (Table 4), and binding to C5aRs expressed on the surface of human PMNs (Table 5). Constructs in which the HBsAg CTL epitope was attached to the N-terminus of the C5a agonist, IPQSLDSWWTSLYSFKPMPLaR (SEQ ID NO:13), IPQSLDSWWTSLRRYSFKPMPLaR (SEQ ID NO:14), and IPQSLDSWWTSLRVRRYSFKPMPLaR (SEQ ID NO:15) behaved as full agonists relative to natural C5a with potencies and C5aR binding affinities comparable to or greater than YSFKPMPLaR (SEQ ID NO:1). In contrast, the construct in which the functionally important C-terminal carboxyl group of the C5a agonist moiety was blocked with the HBsAg CTL epitope YSFKPMPLaR-RRIPQSLDSWWTSL (SEQ ID NO:16) was significantly less potent in umbilical artery contraction (Table 3), inactive in MPO release from PMNs (Table II), and bound poorly to the C5aR (Table 5) relative to both natural C5a and YSFKPMPLaR (SEQ ID NO:1). Similarly, the construct in which a Gly residue blocked the C-terminal carboxyl group of the agonist moiety IPQSLDSWWTSLRRYSFKPMPLaRG (SEQ ID NO:17) was significantly less potent than its C5a-active counterparts in umbilical artery contraction (Table 3) and bound with significantly less affinity to the C5aR (Table 5). This construct was unable to induce a full response relative to natural C5a in MPO release from PMNs (Table 4).

CTL responses are induced in mice when the $L^d$ MHC class I restricted peptide, $S_{28-39}$, of HBsAg is covalently attached to the N-terminus of the C5a agonist via an Arg-Arg linkage. Initial experiments were designed to evaluate CTL induction by the free $L^d$ MHC class I-restricted peptide $S_{28-39}$, IPQSLDSWWTSL (SEQ ID NO:12), the same peptide with two Arg residues added to the C-terminus, IPQSLDSWWTSLRR (SEQ ID NO:18), the free C5a agonist, YSFKPMPLaR (SEQ ID NO:1), and admixtures of the above peptides. Of particular interest was the evaluation of C5a-active constructs in which the HBsAg CTL epitope was covalently attached either directly to the N-terminus of the C5a agonist IPQSLDSWWTSLYSFKPMPLaR (SEQ ID NO:13) or through the double-Arg, protease-sensitive linker IPQSLDSWWTSLRRYSFKPMPLaR (SEQ ID NO:14). The administered amounts of the latter two constructs were adjusted to reflect amounts equal (by weight) to that of the free HBsAg CTL epitope based on relative molecular mass. Mice in each group received two injections, spaced 21 days apart, of the indicated construct. Mice in each group were tested for splenic CTL activity at day 42 as described in Materials and Methods. As shown in Table 6, only the group injected with the double-Arg-linked construct IPQSLDSWWTSLRRYSFKPMPLaR (SEQ ID NO:14) exhibited a significant CTL response against the P815S transfected target cells.

C5a agonist activity is necessary for the induction of Ag-specific CTL responses. To evaluate the necessity of C5a agonist activity in the induction of Ag-specific CTL responses, mice were immunized with C5a-active and C5a-inactive HBsAg CTL epitope-containing constructs. C5a-active constructs were generated by the covalent attachment, via the protease-sensitive, double-Arg linker sequence, of the HBsAg CTL epitope to the N-terminus of the C5a agonist IPQSLDSWWTSLRRYSFKPMPLaR (SEQ ID NO:14). C5a-inactive constructs were generated by blocking the functionally important carboxyl group on the C-terminal Arg of the C5a agonist with either the HBsAg YSFKPMPLaRRRIPQSLDSWWTSL (SEQ ID NO:16) or a Gly residue IPQSLDSWWTSLRRYSFKPMPLaRG (SEQ ID NO:17). The double-Arg-containing HBsAg CTL epitope IPQSLDSWWTSLRR (SEQ ID NO:18) was used as a control. As shown in FIG. 1, only mice that were immunized with the C5a-active construct IPQSLDSWWTSLRRYSFKPMPLaR (SEQ ID NO:14) generated an Ag-specific CTL response. The phenotype of the effector cells responsible for the in vitro cytolytic activity in these experiments was determined to be $CD8^+$ as judged by the ability of a rat anti-mouse lyt 2.2 MAb (2.43, ATCC TIB-210) to almost completely inhibit (greater than 90% inhibition) the cytolytic process. In contrast, a rat anti-mouse L3T4 monoclonal antibody (GK1.5, ATCC TIB-207) known to block $CD4^+$T cell activity had no effect on the in vitro cytolysis induced by the active constructs (data not shown).

CTL responses are induced only by C5a-active constructs containing a protease-sensitive linker sequence between epitope and C5a agonist. To evaluate the requirement for a protease-sensitive linkage between the HBsAg CTL epitope and the C5a agonist for CTL induction, mice were immunized with C5a-active constructs in which the HBsAg CTL epitope was covalently attached directly to the N-terminus of the C5a agonist IPQSLDSWWTSLYSFKPMPLaR (SEQ ID NO:13) or separated by protease-sensitive linker sequences IPQSLDSWWTSLRRYSFKPMPLaR (SEQ ID NO:14) and IPQSLDSWWTSLRVRRYSFKPMPLaR (SEQ ID NO:15). As noted previously, the double-Arg (RR) sequence is sensitive to cleavage by proteases of the subtilisin family and other trypsin-like proteases. The RVRR (SEQ ID NO:19) sequence is a motif recognized by the intracellular protease furin. The results shown in FIG. 2 indicate that of the three C5s-active constructs, only those containing the protease-sensitive linker sequence between the HBsAg CTL epitope and the C5a agonist were capable of inducing an Ag-specific CTL response in mice. Although the RVRR (SEQ ID NO:19)-containing construct was able to elicit a specific CTL response that was significantly above background levels, the response did not exhibit an enhanced magnitude of lysis or more rapid kinetics of induction when compared with that of the RR-containing construct (data not shown). This finding suggests that intracellular furin likely plays a less significant role, or perhaps no role, in the processing of the epitope-C5a agonist construct than other intracellular proteases with specificity for basic or dibasic residues.

Abs to the HBsAg CTL epitope or the C5a agonist are not produced by immunization with the HBsAg CTL epitope-C5a agonist constructs. Previous studies showed that immunization of mice in the presence of additional adjuvant with MUC1 epitope-C5a agonist and opioid receptor epitope-C5a agonist constructs (see previous examples) induced Ab responses to the MUC1 and opioid receptor epitopes and the full-length, intact proteins. Thus, it was of interest to determine whether sera from mice immunized with the control peptides and epitope-C5a agonist constructs contained Ab directed against any of the peptides. Mice were bled at various times following injection and the sera from all groups were tested by ELISA for reactivity with YSFKPMPLaR (SEQ ID NO:1), IPQSLDSWWTSL (SEQ ID NO:12), IPQSLDSWWTSLRR (SEQ ID NO:18), and IPQSLDSWWTSLRRYSFKPMPLaR (SEQ ID NO:14). These analyses failed to show binding to either the C5a agonist or the CTL epitopes (optical densities equal to normal mouse serum at a 1:50 dilution of the serum). However, sera taken from mice following three injections of IPQSLDSWWTSLRRYSFKPMPLaR (SEQ ID NO:14) yielded an ELISA titer of 1:1600 against the immunizing peptide, but did not bind the free peptides IPQSLDSWWTSLRR (SEQ ID NO: 18) or YSFKPMPLaR (SEQ ID NO:1). These results suggest that the C5a-active, RR-containing construct contributes to the formation of a neo-B cell epitope that is presented via the class II pathway.

TABLE 3

Immunogen Activity in Smooth Muscle Contraction of Human Umbilical Artery

| Peptide (SEQ ID NO:) | $pD_2$ ± SE[a] | $EC_{50}$ (μM)[b] | n |
|---|---|---|---|
| C5a | 8.77 ± 0.14 | 0.002 | 3 |
| YSFKPMPLaR(1) | 6.99 ± 0.22 | 0.010 | 3 |
| *IPQSLDSWWTSL*YSFKPMPLaR(12) | 6.68 ± 0.17 | 0.21 | 3 |
| *IPQSLDSWWTSL***RR**YSFKPMPLaR(13) | 6.79 ± 0.31 | 0.161 | 3 |
| YSFKPMPLaR**RR***IPQSLDSWWTSL*(14) | 4.41 ± 0.06* | 39.4 | 3 |
| *ISPSLDSWWTSL***RR**YSFKPMPLaRG(17) | 5.17 ± 0.13* | 6.78 | 3 |
| *ISPSLDSWWTSL***RVRr**YSFKPMPLaRG(15) | 6.67 ± 0.22 | 0.18 | 3 |

[a]$pD_2 = -\log EC_{50}$ (M) expressed as mean ± SE
[b]$EC_{50}$, concentration of peptide resulting in 50% maximum contraction
n represents the number of measurements performed
*significant change from YSFKPMPLaR (SEQ ID NO: 1), $P < 0.05$

TABLE 4

Immunogen Activity in MPO Release from Human PMNs

| Peptide (SEQ ID NO:) | $pD_2 \pm SE^a$ | $EC_{50}$ (μM)[b] | n |
|---|---|---|---|
| C5a | 8.50 ± 0.39 | 0.003 | 3 |
| YSFKPMPLaR(1) | 5.88 ± 0.17 | 1.32 | 3 |
| *IPQSLDSWWTSL***RR**YSFKPMPLaR(13) | 5.80 ± 0.04 | 1.58 | 3 |
| YSFKPMPLaR**RR***IPQSLDSWWTSL*(14) | 6.27 ± 0.29 | 0.54 | 3 |
| YSFKPMPLaR**RR***IPQSLDSWWTSL*(16) | >3 | >1 Mm | 3 |
| *ISPSLDSWWTSL***RR**YSFKPMPLaRG(17) | 5.59 ± 0.28[†] | 2.56 | 3 |
| *ISPSLDSWWTSL***RVRr**YSFKPMPLaRG(15) | 5.61 ± 0.19 | 2.15 | 3 |

[a]$pD_2 = -\log EC_{50}$ (M) expressed as mean ± SE
[b]$EC_{50}$, concentration of peptide resulting in 50% maximum release of myeloperoxidase
n represents the number of measurements performed
[†]This peptide displayed partial agonist activity up to 1 mM achieving 49 ± 9% of the maximum C5a-induced enzyme release (P > 0.05) compared to YSFKPMPLaR (SEQ ID NO: 1).

TABLE 5

Immunogen Binding Affinity for C5aRs on Human PMNs

| Peptide (SEQ ID NO:) | $pD_2 \pm SE^a$ | $EC_{50}$ (μM)[b] | n |
|---|---|---|---|
| C5a | 9.43 ± 0.11 | 0.0004 | 3 |
| YSFKPMPLaR(1) | 5.63 ± 0.10 | 2.34 | 3 |
| *IPQSLDSWWTSL***RR**YSFKPMPLaR(13) | 5.43 ± 0.16 | 3.69 | 3 |
| YSFKPMPLaR**RR***IPQSLDSWWTSL*(14) | 6.38 ± 0.17* | 0.416 | 3 |
| YSFKPMPLaR**RR***IPQSLDSWWTSL*(16) | 3.33 ± 0.09* | 465 | 3 |
| *ISPSLDSWWTSL***RR**YSFKPMPLaRG(17) | 4.77 ± 0.33* | 17.0 | 3 |
| *ISPSLDSWWTSL***RVRr**YSFKPMPLaRG(15) | 6.28 ± 0.14* | 0.529 | 3 |

[a]$pD_2 = -\log EC_{50}$ (M) expressed as mean ± SE
[b]$EC_{50}$, concentration of peptide resulting in 50% inhibition of $^{125}$I-C5 binding
n represents the number of measurements performed
*significant change from YSFKPMPLaR (SEQ ID NO: 1), P < 0.05

TABLE 6

Percent Specific Lysis of $^{51}$Cr-Labeled P815S Target Cells from Mice Immunized with Various HBsAg CTL Epitope/C5a Agonist Peptides.

| Peptide (SEQ ID NO:)(μg injected)[b] | % Specific Lysis[a] Effector: Target Ratio 50:1 | 25:1 | 12.5:1 | 6.25:1 |
|---|---|---|---|---|
| *IPQSLDSWWTSL*(12)(25) | 7 | 5 | 3 | 3 |
| *IPQSLDSWWTSL*YSFKPMPLaR(13)(47) | 6 | 4 | 2 | 1 |
| *IPQSLDSWWTSL***RR**(18)(25) | 2 | 2 | 1 | 0 |
| *IPQSLDSWWTSL***RR**YSFKPMPLaR(14)(42) | 32 | 23 | 14 | 9 |
| YSFKPMPLaR(12)(25) | 1 | 2 | 0 | 0 |
| *IPQSLDWWTSL*(25) + YSFKPMPLaR(25) | 1 | 2 | 1 | 1 |
| *IPQSLDSWWTSL***RR**(25) + YSFKPMPLaR(25) | 2 | 0 | 0 | 0 |
| Normal Spleen Cells | 1 | 1 | 1 | 0 |

[a]The CTL response was measured against the $H2^d$ cell line (P815S) a transfectant that expresses the HBsAg. Normal P815 cells were used as a measure of non-specific lysis. % lysis against $^{51}$Cr-labeled P815 targets ranged between 0–5% at a 50:1 effector-to-target ratio (data not shown).
[b]BALB/c mice were injected s.c. with the indicated peptides in PBS. Mice were boosted on day 21 and spleen cell suspensions from each group were prepared on day 42 and restimulated as in vitro cultures for 4 days in the presence of the HBsAg $S_{28-39}$ peptide, *IPQSLDSWWTSL* (SEQ ID NO: 25).

Discussion:

As can be seen from the results presented above, the conformationally biased C5a agonist YSFKPMPLaR (SEQ. ID NO:1) serves as an effective molecular adjuvant, in this case by inducing Ag-specific CTL responses were $CD8^+$ and were observed only in mice that were immunized with C5a-active constructs in which the HBsAg CTL epitope was covalently attached to the N-terminus of YSFKPMPLaR (SEQ ID NO:1) (i.e., IPQSLDSWWTSLRRYSFKKPM-PLaR (SEQ ID NO:14) and IPQSLDSWWTSLRVRRYS-FKP-MPLaR (SEQ ID NO:15)). This arrangement leaves the biologically important conformational features in the C-terminal region of YSFKPMPLaR (SEQ ID NO:1) free to interact with C5aRs expressed on the cells involved in the immune response and underscores the necessity of C5a agonist activity in the generation of the observed CTL responses. However, the presence of C5a agonist activity in the eptiope-C5a agonist constructs alone was not sufficient in generating a HBsAg-specific CTL response. This was indicated by the lack of a CTL response in mice immunized with IPQSLDSWWTSLYSF-KPMPLaR (SEQ ID NO:13), despite the fact that this construct behaved as a full agonist of C5a. It is noteworthy that this C5a-active construct lacked a protease-sensitive linker sequence separating the epitope moiety from the C5a agonist moiety that was present in the two C5a-active constructs that generated a CTL response—either the double-Arg (RR) or the furin protease-specific sequence RVRR (SEQ ID NO:19). That CTL responses were observed only in mice immunized with C5a-active constructs that contained these protease-sensitive sequences between the epitope and C5a agonist moieties supports the concept that during the internalization of the C5aR/ligand complex an intracellular cleavage event may separate the epitope from the agonist to facilitate the entry of the epitope into intracellular Ag presentation pathways. It should be noted that the failure of the free HBsAg peptide epitope to elicit a CTL response could be attributable to degradation after injection and internalization. Thus, it might be considered that the attachment of the epitope peptide to the N-terminus of the RR-containing C5a agonist peptide might, in part, reduce the sensitivity of the epitope to degradative effects. Such stabilization of the CTL epitope could, in part, contribute to the effectiveness of the co-linear RR-containing constructs. However, it is unlikely that such a phenomenon represents the sole mechanism involved since blocking the C-terminus of the C5a agonist moiety in these constructs abrogates their ability in the observed responses.

It is also noteworthy that the C5a-active constructs IPQSLDSWWTSLRRYSFKPMPLaR (SEQ ID NO:14) and IPQSLDSWWTSLRVRRYSFKPMPLaR (SEQ ID NO:15) induced robust CTL activity after a 2° boost in the absence of any added adjuvant. This observation suggests that the C5a agonist moiety is capable of eliciting the T cell help necessary to induce the observed $CD8^+$ CTL response. It is likely that this T cell involvement emanates from the ability of the C5a agonist moiety to induce the release of immunopotentiating cytokines from C5aR-bearing APCs with which the epitope-C5a agonist constructs interact. This supposition is supported by the fact that C5a has been shown to induce the synthesis and release of IL-β, IL-20), IL-8, and IL-12 from human monocytes and Il-1β, IL-6, IL-8, IL-12, TNF-α, and IFN-γ from human dendritic cells. The C5a agonist moiety, therefore, appears capable of both targeting the attached epitope to C5aR-bearing APCs and eliciting the appropriate immunopotentiating activity. Thus, the YSFKPMPLaR (SEQ ID NO:1) moiety of the constructs used in these immunizations can be viewed as a molecular entity that embodies adjuvant properties characteristic of both a "targeting vehicle" and an "immunomodulator". Finally, mice immunized with YSFKPMPLaR (SEQ ID NO:1)-containing constructs displayed no outward physical signs that would be characteristic of a C5a-mediated anaphylactic response. This in vivo use of YSFKPMPLaR (SEQ ID NO:1) and lack of associated toxicity is consistent with the response-selective activities that have been observed in vitro.

The results described herein are consistent with a mechanism described in the previous examples. The YSFKPMPLaR (SEQ ID NO:1) moiety of the HBsAg constructs interacts with C5aRs expressed on the surface of APCs to induce the synthesis and release of cytokines that activate T cells. Following C5aR activation and cytokine release, the C5aR/ligand complex internalizes allowing intracellular proteases to separate the HBsAg epitope from the C5a agonist by cleaving at the double-Arg (RR) or furin-specific sequence (RVRR) (SEQ ID NO:19) that separate these two moieties. The HBsAg epitope then associates with MHC class I determinants that are subsequently expressed on the APC surface. While this mechanism of CTL induction by the C5a agonist-containing constructs remains is but one of several possibilities, it may involve a novel pathway of exogenous MHC class I Ag presentation. Since it had been generally assumed that class I-mediated Ag presentation involved the generation of peptides from endogenously synthesized proteins, the finding that extracellular soluble proteins could be taken up by professional phagocytes (macrophages and dendritic cells), processed in the cytoplasm or perhaps endosomes to yield antigenic peptides, which are presented in association with MHC class I molecules, is of considerable significance. Presentation of extracellular Ags would be expected to be most efficient when they are particulate in nature and, consequently, are more susceptible to phagocytosis by macrophages and dendritic cells. In the case of the C5a agonist constructs, it is possible that targeting to the C5aR on such cells might accomplish a smilar enhancement of presentation in the MHC class I pathway. Such a proposal seems especially tenable in light of the recent findings that subunits of several bacterial toxins, especially anthrax toxin, when coupled to protein and peptide Ags, are capable of effecting internalization of the Ags and delivering them into the class I presentation pathway with resultant Ag-specific CTL production. Finally, it is noteworthy that a protesome-independent, furin-dependent viral Ag processing pathway where cleavage occurs in the Golgi or post-Goli secretory pathway has been recently described. Again, this finding suggests that intersection of internalized Ags/peptides with elements of the anterograde secretory pathway (endosomal or trans-Golgi region), as may occur with C5aR/ligand complexes, could result in processing events and association with unoccupied class I molecules that are in transit through this pathway.

Although an exogenous pathway of intracellular processing of the epitope-RR-C5a agonist constructs appears to be a plausible mechanism, it is also possible that the HBsAg epitope peptide is introduced onto MHC class I determinants expressed on the surface of the APC. Thus, the co-linear peptides containing the RR-C5a agonist moiety could bind to the surface of APCs and, after proteolytic cleavage of the scissile linkage, the HBsAg CTL epitope could displace lower affinity endogenous peptide in cell surface class I molecules. At present, the relative contribution of extracellular and intracellular processing events in CTL induction mediated by the C5a agonist moiety has not been assessed. Further in vitro experiments are being designed to address this issue.

In contrast to formulating peptide and/or protein Ags as particulates or as toxin subunit-conjugates or other derivatives, the C5a agonist peptide, rather than serving as an inert carrier, might provide the added benefit of delivering immunopotentiating signals. Accordingly, such constructs, containing either covalently linked peptides or proteins, might be of particular benefit in those situations where the target proteins or peptides are nominally immunogenic irrespective of the delivery vehicle or construct employed. In the case of peptides, a further advantage of this technology is that the C5a agonist constructs are relatively simple to produce and do not require recombinant technologies and associated protein purification methodologies or specialized formulation procedures.

The Ag-specific responses to well-defined T cell and B cell epitopes observed in our studies support the potential use of YSFKPMPLaR (SEQ ID NO:1) and other response-selective C5a agonists as molecular adjuvants for inducing a defined spectrum of humoral and/or cellular responses against peptide, protein, and, possibly, non-protein Ags. Such a possibility would provide a broad-based adjuvant/delivery technology that would be applicable to a number of infectious and oncologic diseases in either prophylactic or therapeutic settings.

While certain preferred embodiments of the present invention have been described and specifically exemplified above, it is not intended that the invention be limited to such embodiments. Various modifications may be made to the invention without departing from the scope and spirit thereof as set forth in the following claims.

We claim:

1. A molecular adjuvant for enhancing an immune response to an immunogen comprising:

a targeting moiety which binds specifically to a receptor on an antigen presenting cell, the targeting moiety being linked to the immunogen by a cleavable linker, whereby binding of the molecular adjuvant to the antigen presenting cell receptor activates the antigen presenting cell, effecting delivery of said immunogen to an antigen presenting pathway of the antigen presenting cell, wherein said targeting moiety binds specifically to a C5a receptor and is selected from the group consisting of C5a, the C-terminal ten residues of C5a, and a peptide agonist analog of the C-terminal ten residues of C5a, and wherein said targeting moiety is at the C-terminus of said molecular adjuvant.

2. The molecular adjuvant of claim 1, wherein the targeting moiety is a peptide comprising the sequence YSFKPMPLaR, which is SEQ ID NO:1.

3. The molecular adjuvant of claim 1, wherein the immunogen comprises at least one substance selected from the group consisting of peptides, proteins, carbohydrates, nucleic acids and lipids.

4. The molecular adjuvant of claim 3, wherein the immunogen comprises a peptide.

5. The molecular adjuvant of claim 4, wherein the peptide is an epitope of human mucin-1.

6. The molecular adjuvant of claim 3, wherein the immunogen comprises a protein.

7. The molecular adjuvant of claim 1, wherein the immunogen comprises a tumor-specific antigen.

8. The molecular adjuvant of claim 1, wherein the cleavable linker comprises an oligopeptide that is cleavable by a protease.

9. The molecular adjuvant of claim 8, wherein the cleavable linker is sensitive to cleavage by a protease of the trypsin family of proteases.

10. The molecular adjuvant of claim 8, wherein the cleavable linker comprises a dibasic dipeptide sequence.

11. The molecular adjuvant of claim 10, wherein the cleavable linker comprises an Arg-Arg dipeptide sequence.

12. The molecular adjuvant of claim 10, wherein the cleavable linker comprises Arg-Val-Arg-Arg (SEQ ID NO:19).

13. A composition for enhancing an immune response to an immunogen in a subject in which the enhanced immune response is desired, the composition comprising the molecular adjuvant of claim 1 in a biologically compatible medium.

14. The molecular adjuvant of claim 3, wherein said peptides are selected from the group consisting of glycopeptides, phosphopeptides, and lipopeptides.

15. The molecular adjuvant of claim 3, wherein said proteins are selected from the group consisting of glycoproteins, phosphoproteins, and lipoproteins.

* * * * *